(12) United States Patent
Ikeda

(10) Patent No.: US 8,036,339 B2
(45) Date of Patent: Oct. 11, 2011

(54) DENTAL COLORIMETRY APPARATUS

(75) Inventor: Yasuto Ikeda, Tachikawa (JP)

(73) Assignee: Olympus Corporation, Tokyo (JP)

( * ) Notice: Subject to any disclaimer, the term of this patent is extended or adjusted under 35 U.S.C. 154(b) by 337 days.

(21) Appl. No.: 12/491,600

(22) Filed: Jun. 25, 2009

(65) Prior Publication Data

US 2009/0322868 A1 Dec. 31, 2009

(30) Foreign Application Priority Data

Jun. 30, 2008 (JP) ................................ 2008-171438
Jun. 1, 2009 (JP) ................................ 2009-132244

(51) Int. Cl.
*H04N 7/18* (2006.01)
*G06K 9/00* (2006.01)

(52) U.S. Cl. ........................................................ 378/77
(58) Field of Classification Search .............. 348/77–79, 348/E7.085; 382/162
See application file for complete search history.

(56) References Cited

U.S. PATENT DOCUMENTS

2007/0140553 A1 6/2007 Katsumata

FOREIGN PATENT DOCUMENTS

| EP | 1 975 870 A1 | 10/2008 |
|---|---|---|
| JP | 2001-188905 A | 7/2001 |
| JP | 3578962 A | 9/2001 |
| JP | 2002-049694 A | 2/2002 |
| JP | 2005-130928 A | 5/2005 |
| JP | 2006-174037 A | 1/2006 |
| JP | 2007-190371 A | 8/2007 |
| WO | WO 2007/083600 A1 | 7/2007 |

OTHER PUBLICATIONS

Japanese Office Action dated Jan. 12, 2010, issued in counterpart Japanese Application No. 2009-132244.
English language translation of a Japanese Office Action dated Jan. 12, 2010 in counterpart Japanese Application No. 2009-132244.
Decision to Grant a Patent dated Sep. 7, 2010, and English translation thereof, issued in counterpart Japanese Application No. 2009-132244.

*Primary Examiner* — Tung Vo
(74) *Attorney, Agent, or Firm* — Holtz, Holtz, Goodman & Chick, P.C.

(57) ABSTRACT

A dental colorimetry apparatus that allows the color balance of an entire row of teeth to be checked is provided. The invention provides a dental colorimetry apparatus 2 including a multiband-image storing section 21 storing images of teeth in association with information about the positions of the teeth in row of teeth; a contour-line extracting section 25 for extracting contour lines of the teeth from the images of the teeth; a rectangle-setting section 27 for setting rectangles in the images of the teeth so as to include the contour lines extracted by the contour-line extracting section 25 and so as to circumscribe at least both sides of the teeth; and an image-generating section 29 for generating a row-of-teeth image by arranging the images of the teeth based on the information about the positions of the teeth in the row of teeth so that the rectangles adjoin each other.

27 Claims, 18 Drawing Sheets

DENTAL COLORIMETRY APPARATUS

BACKGROUND OF THE INVENTION

1. Field of the Invention

The present invention relates to dental colorimetry apparatuses, systems, and methods for colorimetry of patients' teeth and to computer-readable recording media storing dental colorimetry programs.

This application is based on Japanese Patent Application Nos. 2008-171438 and 2009-132244, the content of which is incorporated herein by reference.

2. Description of Related Art

Composite resins are conventionally used as dental fillers for filling cavities formed in teeth due to, for example, tooth decay. When filling a cavity with composite resins, for example, the dentist visually compares the color of the patient's tooth with those of color samples to select a color sample closest in color to the patient's tooth. Each color sample is provided with a table specifying a recommended combination of colors of composite resins used for filling. The dentist refers to the table corresponding to the selected color sample to select the colors of the composite resins used for filling before he or she performs treatment. The color samples are, for example, ceramic pieces with different colors manufactured in the shape of teeth.

In treatment using a ceramic crown, for example, the dentist visually compares the color of the patient's tooth with those of color samples, called shade guides, to select a color sample closest in color to the patient's tooth before he or she performs treatment using a prosthesis prepared based on the selected color sample.

The color samples are, for example, ceramic pieces with different colors manufactured in the shape of teeth.

On the other hand, to alleviate the burden on dentists associated with, for example, selection of a color sample, one proposed technique provides the function of automatically selecting a color sample closest in color to the tooth to aid dentists in selecting the color of a color sample (see, for example, Japanese Unexamined Patent Application, Publication No. 2007-190371).

According to Japanese Unexamined Patent Application, Publication No. 2007-190371, for example, the tooth to be treated and a color sample close in color to the tooth are displayed side by side on a display screen so that the dentist can check their colors etc. on the screen.

BRIEF SUMMARY OF THE INVENTION

The related-art dental colorimetry apparatus disclosed in Japanese Unexamined Patent Application, Publication No. 2007-190371, however, has a problem in that the color balance of an entire row of teeth cannot be checked because only the tooth to be treated is displayed for comparison with the color of the color sample.

In this case, it is possible to perform the color comparison for the row of teeth by separately acquiring images of the individual teeth and displaying the images of the teeth side by side. However, if, for example, an image of a small tooth is acquired, the single image contains not only the tooth to be imaged, but also parts of the adjacent teeth, because the angle of view for image acquisition is fixed and the teeth differ in size. Therefore, an image of the row of teeth generated by arranging such acquired images in order cannot accurately reproduce the row of teeth. This technique therefore has a problem in that it is difficult to check the color balance of the entire row of teeth.

An object of the present invention, which has been made to solve the above problem, is to provide a dental colorimetry apparatus, system, and method that allow the color balance of an entire row of teeth to be checked and a computer-readable recording medium storing a dental colorimetry program that allows the color balance of an entire row of teeth to be checked.

A first aspect of the present invention is a dental colorimetry apparatus including a first storage section storing images of teeth in association with information about the positions of the teeth in row of teeth; a contour-line extracting section for extracting contour lines of the teeth from the images of the teeth; a rectangle-setting section for setting rectangles in the images of the teeth so as to include the contour lines extracted by the contour-line extracting section and so as to circumscribe at least both sides of the teeth; and an image-generating section for generating a row-of-teeth image by arranging the images of the teeth based on the information about the positions of the teeth in the row of teeth so that the rectangles adjoin each other.

According to this configuration, because the contour lines of the teeth are extracted from the images of the teeth and the rectangles are set in the images of the teeth so as to include the contour lines and so as to circumscribe at least both sides of the teeth, the regions of main teeth can be cut out along the rectangles. Hence, even if parts of the adjacent teeth appear in the images of the teeth, the regions of the main teeth can be separated from those of the adjacent teeth by the rectangles. The images of the teeth are then arranged so that the rectangles adjoin each other to generate the row-of-teeth image. Thus, a row-of-teeth image in which the teeth are properly arranged can be generated.

In the above dental colorimetry apparatus, the rectangle-setting section may set the rectangles so as to include the contour lines and so as to circumscribe at least both sides and ends of the teeth, and the image-generating section may generate the row-of-teeth image by arranging the images of the teeth so that edges, adjoining the ends of the teeth, of the rectangles are located at the same height.

If the images of the teeth are arranged in this way, the ends of the teeth can be aligned at the same height. As a result, an easily viewable row-of-teeth image can be provided.

In the above dental colorimetry apparatus, the rectangle-setting section may set the rectangles so as to circumscribe ends of the teeth, and the image-generating section may arrange the images of the teeth so that edges, adjoining the ends of the teeth, of the rectangles are located farther away from a centerline between the top and bottom row of teeth in directions away from the center of the row of teeth along the row of teeth.

In this case, an apparently natural row-of-teeth image can be provided without showing an artificial appearance.

The above dental colorimetry apparatus may further include a second storage section storing information about the relative sizes of the teeth determined from a reference row-of-teeth image; and a contour-correcting section for correcting the contour lines of the teeth based on the information about the relative sizes of the teeth stored in the second storage section.

The sizes of the teeth shown in the images of the teeth vary from tooth to tooth depending on, for example, the conditions during image acquisition. In such a case, the contour lines of the teeth are corrected based on the information about the relative sizes of the teeth determined from the reference row-of-teeth image, so that the scales of the teeth constituting the row of teeth can be adjusted to that of the reference row-of-teeth image. This enhances the reproducibility of the row of teeth.

In the above dental colorimetry apparatus, the images of the teeth stored in the first storage section and the reference row-of-teeth image may be acquired from the same patient.

Thus, because the scales of the patient's individual teeth in the images of the teeth are adjusted based on the information about the relative sizes of the teeth determined from the row-of-teeth image of the same patient, a row-of-teeth image close in scale to the patient's actual row of teeth can be generated.

In the above dental colorimetry apparatus, the rectangle-setting section may set the rectangles using the contour lines corrected by the contour-correcting section.

Thus, because the rectangles are set in the images of the teeth with the corrected contour lines, the process can be simplified as compared with the case where the rectangles are set before both the contour lines and the rectangles are corrected.

The above dental colorimetry apparatus may further include a third storage section storing a plurality of pieces of color information, and, if one of the pieces of color information stored in the third storage section is designated and at least one of the images of the teeth constituting the row-of-teeth image is designated, the designated piece of color information may replace the color of the tooth in the designated image of the tooth.

According to this configuration, some of the teeth constituting the row of teeth can be changed to desired colors. Accordingly, for example, if a dental filler such as a composite resin is to be applied to a defective tooth, the user can check how the tooth will look in the entire row of teeth after treatment. This allows selection of a dental filler or shade guide with a more natural color.

The above dental colorimetry apparatus may further include an image-selecting section for selecting one of the images of the teeth stored in the first storage section; an image-duplicating section for duplicating the image of the tooth selected by the image-selecting section; and an image-updating section for storing the image of the tooth duplicated by the image-duplicating section in the first storage section as a tooth image having different positional information.

By doing so, the image of the tooth selected by the image-selecting section is duplicated by the image-duplicating section and is stored in the first storage section as a tooth image having different positional information by the image-updating section. If the patient's row of teeth include a missing tooth or a defective tooth, such as a decayed tooth, an image of the patient's other healthier tooth can be duplicated and stored as an image having the information about the position of the missing or defective tooth. As a result, a row-of-teeth image virtually showing healthy teeth with the missing or defective tooth replaced can be generated.

The above dental colorimetry apparatus may further include a rectangular-image storing section storing the images of the teeth in which the rectangles are set by the rectangle-setting section in association with the information about the positions of the teeth in the row of teeth; an image-selecting section for selecting one of the images of the teeth stored in the rectangular-image storing section; an image-duplicating section for duplicating the image of the tooth selected by the image-selecting section; and an image-updating section for storing the image of the tooth duplicated by the image-duplicating section in the rectangular-image storing section as a tooth image having different positional information.

By doing so, the images of the teeth in which the rectangles are set are stored in the rectangular-image storing section, while duplicating the images of the teeth in which the rectangles are set. Thus, a row-of-teeth image virtually showing healthy teeth with a missing tooth or a defective tooth, such as a decayed tooth, replaced can be generated without changing the images of the teeth stored in the first storage section or newly setting rectangles in the duplicated images of the teeth.

In the above dental colorimetry apparatus, the image-duplicating section may duplicate the image of the tooth selected by the image-selecting section so as to be vertically or laterally inverted.

By doing so, a missing tooth or a defective tooth, such as a decayed tooth, can be replaced with the image of the tooth located at the position vertically or laterally symmetrical to the position of the missing or defective tooth. As a result, a virtual row-of-teeth image more naturally showing the row of teeth can be generated.

A second aspect of the present invention is a dental colorimetry apparatus including a first storage section storing tooth images containing target teeth and partial adjacent teeth adjacent to the target teeth in association with information about the positions of the target teeth in row of teeth; a contour-line extracting section for extracting contour lines of the target teeth and the adjacent teeth from the tooth images; a rectangle-setting section for setting rectangles in the tooth images so as to include the contour lines of the target teeth extracted by the contour-line extracting section and so as to circumscribe at least both sides of the target teeth; and an image-generating section for generating a row-of-teeth image by arranging portions of the tooth images inside the rectangles based on the information about the positions of the target teeth in the row of teeth so that the rectangles inscribe the contour lines of the adjacent teeth in the adjacent tooth images.

According to this aspect, the image-generating section generates the row-of-teeth image by arranging the portions of the tooth images inside the rectangles so that the rectangles set by the rectangle-setting section so as to circumscribe both sides of the target teeth inscribe the contour lines of the adjacent teeth in the adjacent tooth images extracted by the contour-line extracting section. In the row-of-teeth image thus generated, therefore, the distance between the contour line of the target tooth in a certain tooth image and the contour line of the target tooth in a tooth image adjacent thereto substantially agrees with the distance between the contour lines of the target tooth and one of the adjacent teeth in the certain tooth image or the tooth image adjacent thereto. Accordingly, if a gap or overlap is present between the two adjacent teeth, a row-of-teeth image showing the gap or overlap at that position can be generated. Thus, a row-of-teeth image closer to the patient's row of teeth can be generated.

In the above dental colorimetry apparatus, preferably, the image-generating section arranges the tooth images so that the contour lines of the adjacent teeth in the tooth images substantially coincide with the contour lines of the target teeth in the adjacent tooth images.

By doing so, the positions of the tooth images in the direction along the height of the teeth can be adjusted using the contour lines of the adjacent teeth in the tooth images. As a result, a row-of-teeth image closer to the patient's row of teeth can be generated.

In the above dental colorimetry apparatus, the image-generating section may scale down the tooth images in a direction along the row of teeth so that the contour lines of the target teeth in the tooth images substantially coincide with the contour lines of the adjacent teeth in the adjacent tooth images.

Because the human row of teeth are arch-shaped from front to back, the angle thereof changes gradually from the center of the row of teeth to both sides in the direction along the row of teeth. Hence, simply arranging tooth images acquired in front of the individual teeth results in an unnatural row-of-teeth image. According to the present invention, a more natural row-of-teeth image representing the arch shape can be generated by scaling down the tooth images in the direction along the row of teeth so that the contour lines of the target teeth in the tooth images substantially coincide with the contour lines of the adjacent teeth in the adjacent tooth images.

A third aspect of the present invention is a color colorimetry system including an image-acquisition device for acquiring an image inside an oral cavity and a dental colorimetry apparatus for processing the image acquired by the image-acquisition device. The dental colorimetry apparatus includes a first storage section storing acquired images of teeth in association with information about the positions of the teeth in row of teeth; a contour-line extracting section for extracting contour lines of the teeth from the acquired images of the teeth; a rectangle-setting section for setting rectangles in the acquired images of the teeth so as to include the contour lines extracted by the contour-line extracting section and so as to circumscribe at least both sides of the teeth; an image-generating section for generating a row-of-teeth image by arranging the acquired images of the teeth based on the information about the positions of the teeth in the row of teeth so that the rectangles adjoin each other; and a display section for displaying the row-of-teeth image generated by the image-generating section.

A fourth aspect of the present invention is a dental colorimetry system including an image-acquisition device for acquiring an image inside an oral cavity and a dental colorimetry apparatus for processing the image acquired by the image-acquisition device. The dental colorimetry apparatus includes a first storage section storing tooth images containing target teeth and partial adjacent teeth adjacent to the target teeth in association with information about the positions of the target teeth in row of teeth; a contour-line extracting section for extracting contour lines of the target teeth and the adjacent teeth from the tooth images; a rectangle-setting section for setting rectangles in the tooth images so as to include the contour lines of the target teeth extracted by the contour-line extracting section and so as to circumscribe at least both sides of the target teeth; an image-generating section for generating a row-of-teeth image by arranging portions of the tooth images inside the rectangles based on the information about the positions of the target teeth in the row of teeth so that the rectangles inscribe the contour lines of the adjacent teeth in the adjacent tooth images; and a display section for displaying the row-of-teeth image generated by the image-generating section.

A fifth aspect of the present invention is a dental colorimetry method including the steps of extracting contour lines of teeth from images of the teeth associated with information about the positions of the teeth in row of teeth; setting rectangles in the images of the teeth so as to include the extracted contour lines and so as to circumscribe at least both sides of the teeth; and generating a row-of-teeth image by arranging the images of the teeth based on the information about the positions of the teeth in the row of teeth so that the rectangles adjoin each other.

A sixth aspect of the present invention is a dental colorimetry method including the steps of extracting contour lines of target teeth and partial adjacent teeth adjacent to the target teeth from tooth images containing the target teeth and the adjacent teeth and associated with information about the positions of the target teeth in row of teeth; setting rectangles in the tooth images so as to include the extracted contour lines of the target teeth and so as to circumscribe at least both sides of the target teeth; and generating a row-of-teeth image by arranging portions of the tooth images inside the rectangles based on the information about the positions of the target teeth in the row of teeth so that the rectangles inscribe the contour lines of the adjacent teeth in the adjacent tooth images.

A seventh aspect of the present invention is a computer-readable recording medium storing a dental colorimetry program for instructing a computer to execute a process including the steps of extracting contour lines of teeth from images of the teeth associated with information about the positions of the teeth in row of teeth; setting rectangles in the images of the teeth so as to include the extracted contour lines and so as to circumscribe at least both sides of the teeth; and generating a row-of-teeth image by arranging the images of the teeth based on the information about the positions of the teeth in the row of teeth so that the rectangles adjoin each other.

An eighth aspect of the present invention is a computer-readable recording medium storing a dental colorimetry program for instructing a computer to execute a process including the steps of extracting contour lines of target teeth and partial adjacent teeth adjacent to the target teeth from tooth images containing the target teeth and the adjacent teeth and associated with information about the positions of the target teeth in row of teeth; setting rectangles in the tooth images so as to include the extracted contour lines of the target teeth and so as to circumscribe at least both sides of the target teeth; and generating a row-of-teeth image by arranging portions of the tooth images inside the rectangles based on the information about the positions of the target teeth in the row of teeth so that the rectangles inscribe the contour lines of the adjacent teeth in the adjacent tooth images.

The present invention provides the advantage that the color balance of an entire row of teeth can be checked.

DETAILED DESCRIPTION OF THE INVENTION

Dental colorimetry apparatuses, dental colorimetry systems, dental colorimetry methods, and dental colorimetry programs according to embodiments of the present invention will now be described with reference to the drawings.

Figure 1:
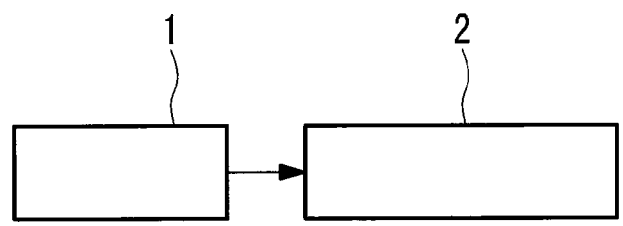
FIG. 1 is a diagram showing the overall configuration of a dental colorimetry apparatus according to a first embodiment of the present invention.

As shown in FIG. 1, a dental colorimetry system according to a first embodiment of the present invention includes an image-acquisition device 1 and a dental colorimetry apparatus 2.

The image-acquisition device 1 is, for example, the one disclosed in Japanese Unexamined Patent Application, Publication No. 2007-190371, having a normal image acquisition mode for acquiring an RGB image, that is, a normal function of digital cameras, and a multiband image acquisition mode.

In the multiband image acquisition mode, a plurality of RGB images are acquired by sequentially irradiating the subject with light in different wavelength bands sequentially emitted from a plurality of light sources, accommodated in the image-acquisition device 1, that emit light in different wavelength bands. A B image is selected from the RGB image acquired when light is emitted from the light source that emits light whose central wavelength falls in the blue wavelength band. A G image is selected from the RGB image acquired when light is emitted from the light source that emits light whose central wavelength falls in the green wavelength band. An R image is selected from the RGB image acquired when light is emitted from the light source that emits light whose central wavelength falls in the red wavelength band. The selected R, G, and B images are combined to generate a multispectral image. The number of wavelength bands of the light emitted from the light sources is preferably four or more.

Of the above two image acquisition modes, the normal image acquisition mode is used to acquire an image of a wide area, for example, to acquire an image of the patient's entire row of teeth or to acquire an image of his or her entire jaw. The multiband image acquisition mode, on the other hand, is used to accurately measure the color of one or two of the patient's teeth, that is, for colorimetry of the teeth.

In this embodiment, for example, the image-acquisition device 1 acquires an image of the patient's entire row of teeth in the normal image acquisition mode and separately acquires images of the patient's individual teeth in the multiband image acquisition mode.

The image of the patient's entire row of teeth and the multiband images of the individual teeth acquired by the image-acquisition device 1 are transmitted to the dental colorimetry apparatus 2 via, for example, a transmission medium and are stored in a database included in the dental colorimetry apparatus 2. The acquired images may instead be stored in the dental colorimetry apparatus 2 via an auxiliary storage unit such as a USB memory.

Figure 2:
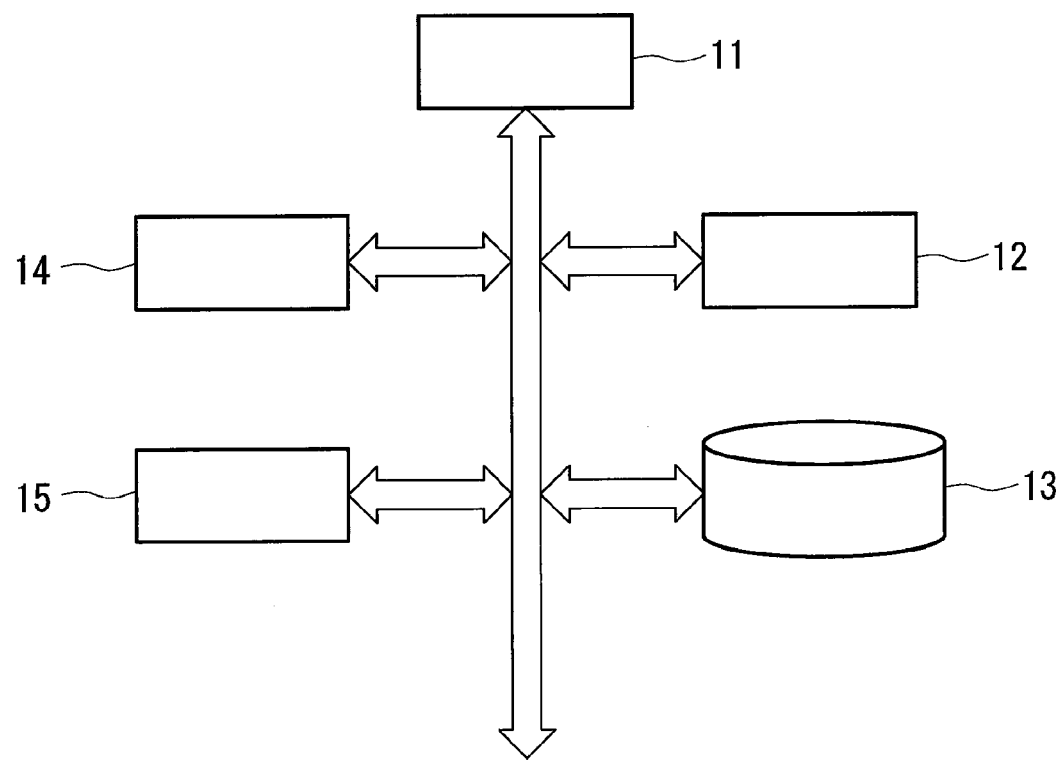
FIG. 2 is a diagram showing the hardware configuration of a dental colorimetry apparatus in FIG. 1.

The dental colorimetry apparatus 2 is a computer system (a computer system) including, for example, as shown in FIG. 2, a central processing unit (CPU) 11, a main storage unit 12 such as a random access memory (RAM), an auxiliary storage unit 13, an input unit 14 such as a keyboard and a mouse, and a display unit 15 such as a liquid crystal display.

The auxiliary storage unit 13 is a computer-readable recording medium such as a magnetic disk, a magneto-optical disk, a CD-ROM, a DVD-ROM, or a semiconductor memory. The auxiliary storage unit 13 stores various programs such as a dental colorimetry program. The CPU 11 reads the programs from the auxiliary storage unit 13 into the main storage unit 12, such as a RAM, to execute the programs, thus implementing processes in individual sections, as described below.

Figure 3:
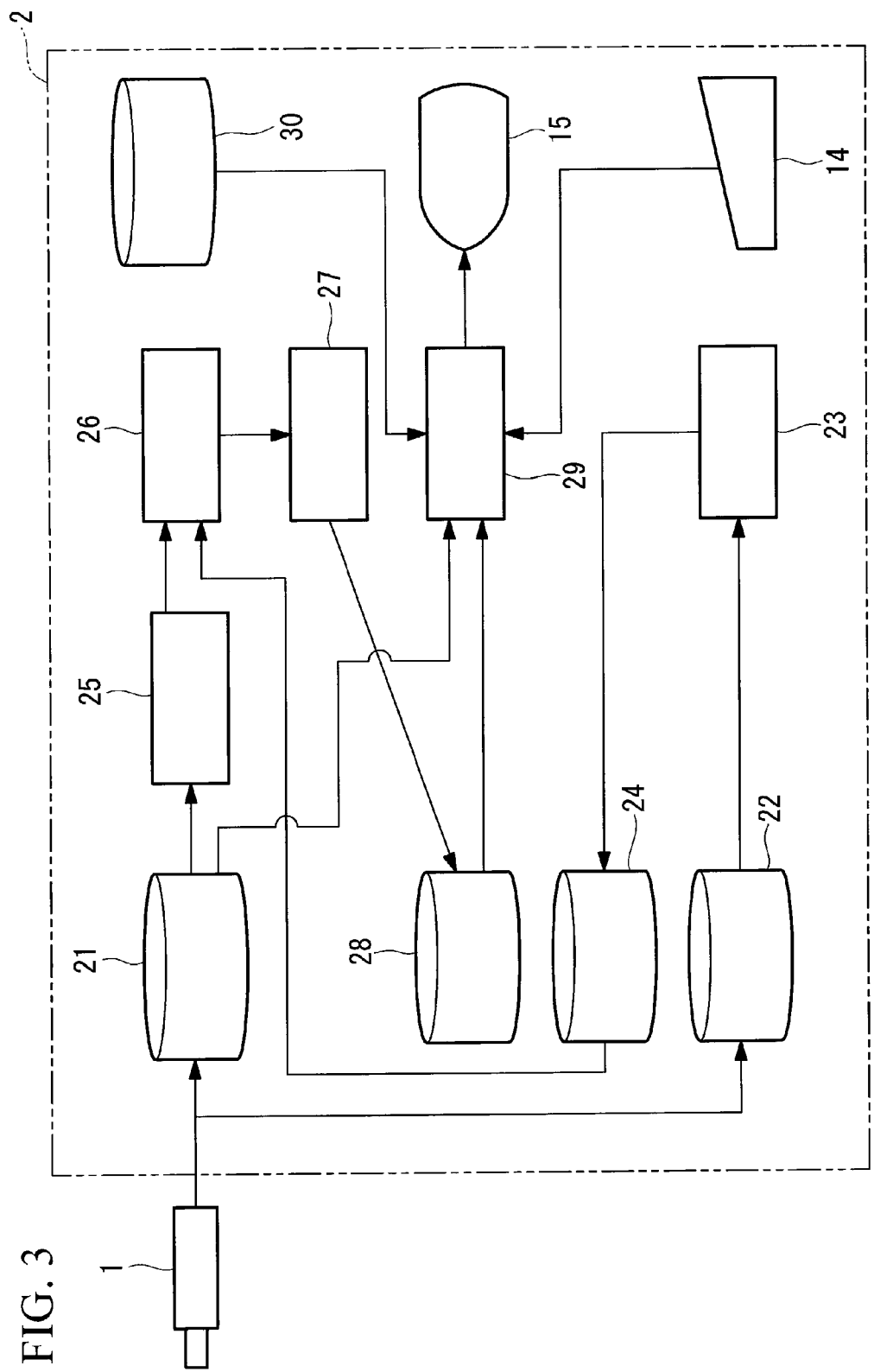
FIG. 3 is a functional block diagram of the dental colorimetry apparatus in FIG. 1.

FIG. 3 is a functional block diagram showing functions implemented in the dental colorimetry apparatus 2. As shown in FIG. 3, the dental colorimetry apparatus 2 mainly includes a multiband-image storing section (first storage section) 21, a row-of-teeth-image storing section 22, a relative-tooth-size calculating section 23, a relative-ratio storing section (second storage section) 24, a contour-line extracting section 25, a contour-correcting section 26, a rectangle-setting section 27, a rectangular-image storing section 28, an image-generating section 29, and a shade-guide storing section (third storage section) 30.

The multiband-image storing section 21 stores the images of the teeth acquired by the image-acquisition device 1 in the multiband image acquisition mode in association with the tooth numbers thereof. The tooth numbers are numbers indicating the positions of the respective teeth in the row of teeth.

The row-of-teeth-image storing section 22 stores the image of the patient's row of teeth acquired by the image-acquisition device 1 in the normal image acquisition mode.

The relative-tooth-size calculating section 23 calculates the relative height ratio (relative size information) of each tooth from the row-of-teeth image stored in the row-of-teeth-image storing section 22. Specifically, the relative-tooth-size calculating section 23 extracts the contour line of each tooth from the row-of-teeth image and then acquires tooth height information.

For example, the contour line of each tooth may be automatically extracted by executing a built-in contour-line-extracting program. As another example, the dentist may display the row-of-teeth image on the display unit 15 and set contour lines therein by tracing the contour line of each tooth using a device such as a pointing pen. The contour line of each tooth may be extracted by a known technique, and the technique used is not specifically limited. For example, a technique for identifying a tooth region disclosed in Japanese Unexamined Patent Application, Publication No. 2007-190371 (see paragraphs [0081] to [0087]) can be used as the method for automatically extracting a contour line. It is also possible to use, for example, a contour detection method disclosed in the specification of Japanese Patent Application No. 2007-069227, previously filed by the present assignee.

Figure 4:
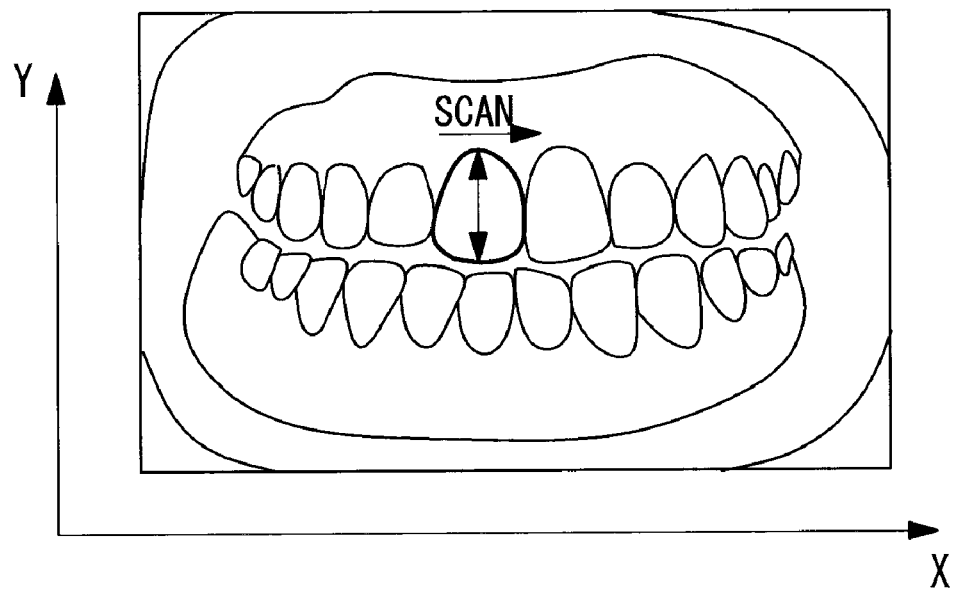
FIG. 4 is a diagram for explaining a method for obtaining tooth height information from a row-of-teeth image.

As shown in FIG. 4, for example, the tooth height information is acquired by, assuming that an XY orthogonal coordinate system is set in the row-of-teeth image, scanning, along the X axis, a line segment extending parallel to the Y axis from one end to the other end of a tooth to determine the maximum length of the line segment as the height of the tooth. This process is executed for each tooth to acquire the tooth height information for each tooth. Subsequently, a tooth representing the teeth constituting the row of teeth (hereinafter referred to as a "representative tooth") is selected, and the ratio of the height of each tooth to that of the representative tooth is determined. Thus, the height ratio of each tooth to the representative tooth is calculated.

The relative-tooth-size calculating section 23 calculates the relative height ratio of each tooth and stores the relative height ratio in association with the tooth number thereof in the relative-ratio storing section 24, and also stores the tooth number of the representative tooth in the relative-ratio storing section 24.

The contour-line extracting section 25 reads the image of each tooth from the multiband-image storing section 21 and extracts the contour line of the tooth from the image of the tooth. As with the contour extraction in the relative-tooth-size calculating section 23, the contour line of each tooth may be extracted by a known method. Alternatively, the dentist may display the image of each tooth on the display unit 15 and input a contour line therein.

The contour-correcting section 26 corrects the contour line of each tooth extracted by the contour-line extracting section 25 using the relative height ratio stored in the relative-ratio storing section 24. For example, if the tooth number is "2", the relative height ratio is "0.8", and the tooth number of the representative tooth is "1", the contour-correcting section 26 corrects the contour line of tooth number "2" so that the height of the contour line of tooth number "2" is 0.8 times the height determined from the contour line of the representative tooth, namely, tooth number "1". The contour-correcting section 26 thus executes correction on each tooth using the relative height ratio thereof.

Figure 5:
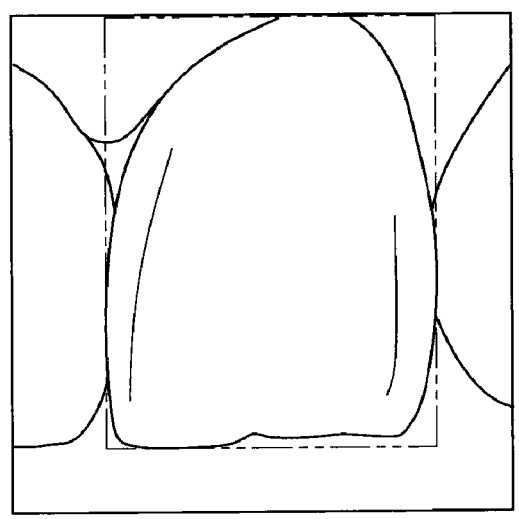
FIG. 5 is a diagram showing a rectangular region set in a tooth image.

The rectangle-setting section 27 sets a rectangular region in the image of each tooth based on the contour line of the tooth corrected by the contour-correcting section 26. Specifically, the rectangle-setting section 27 sets a rectangle including the contour line and circumscribing at least both sides of the tooth. In this case, preferably, the rectangle-setting section 27 sets a rectangle including the contour line and circumscribing at least both sides and the end of the tooth. As a result, for example, a rectangle as shown in FIG. 5 is set in the image of the tooth.

The rectangular-image storing section 28 stores information about the rectangular region set in the image of each tooth in association with the tooth number thereof. The rectangular-image storing section 28 stores, for example, information about the position of the rectangular region, that is, information indicating where the rectangular region is set in the image of the tooth.

The image-generating section 29 reads the information about the rectangular regions stored in the rectangular-image storing section 28 and the tooth images stored in the multiband-image storing section 21 and superimposes the rectangular regions on the respective tooth images. The image-generating section 29 then generates a row-of-teeth image by arranging the tooth images based on the tooth numbers thereof and displays it in a predetermined display area on the display unit 15.

Specifically, the image-generating section 29 generates a row-of-teeth image by arranging the tooth images so that the rectangular regions set in the tooth images adjoin each other. In this case, preferably, the image-generating section 29 arranges the tooth images so that the edges, adjoining the ends of the teeth, of the rectangular regions are located at the same height. If the tooth images are arranged in this way, the ends of the teeth are aligned, thus providing an easily viewable row-of-teeth image.

In addition, preferably, the image-generating section 29 superimposes the tooth images so that the portions of the tooth images inside the rectangular regions come in front and the portions outside the rectangular regions go behind. This allows a row-of-teeth image in which the individual teeth are neatly arranged to be generated, while maintaining the information about the portions outside the rectangular regions.

The shade-guide storing section 30 stores color information about individual shade guides in association with the identification numbers thereof. The shade guides are, for example, ceramic pieces with different colors manufactured in the shape of teeth. The color information refers to, for example, colorimetry information (such as RGB values, L*a*b* values, CMYK values, XYZ values, L*u*v* values, or L*C*h values), reflection spectra, or spectral radiant intensities obtained from images of the shade guides acquired in the multiband image acquisition mode.

For example, if the user checking the row-of-teeth image displayed on the display unit 15 manipulates the input unit 14 to designate the identification number of a certain shade guide and at least one of the tooth images displayed as the row-of-teeth image, the image-generating section 29 reads color information about the shade guide designated by the user from the shade-guide storing section 30 and displays the color of the shade guide on the display unit 15 so as to replace the color information about the tooth designated by the user. This allows the color of any tooth constituting the row of teeth to be changed to the color of a desired shade guide.

Next, the operation of the above dental colorimetry system will be described.

Figure 6:
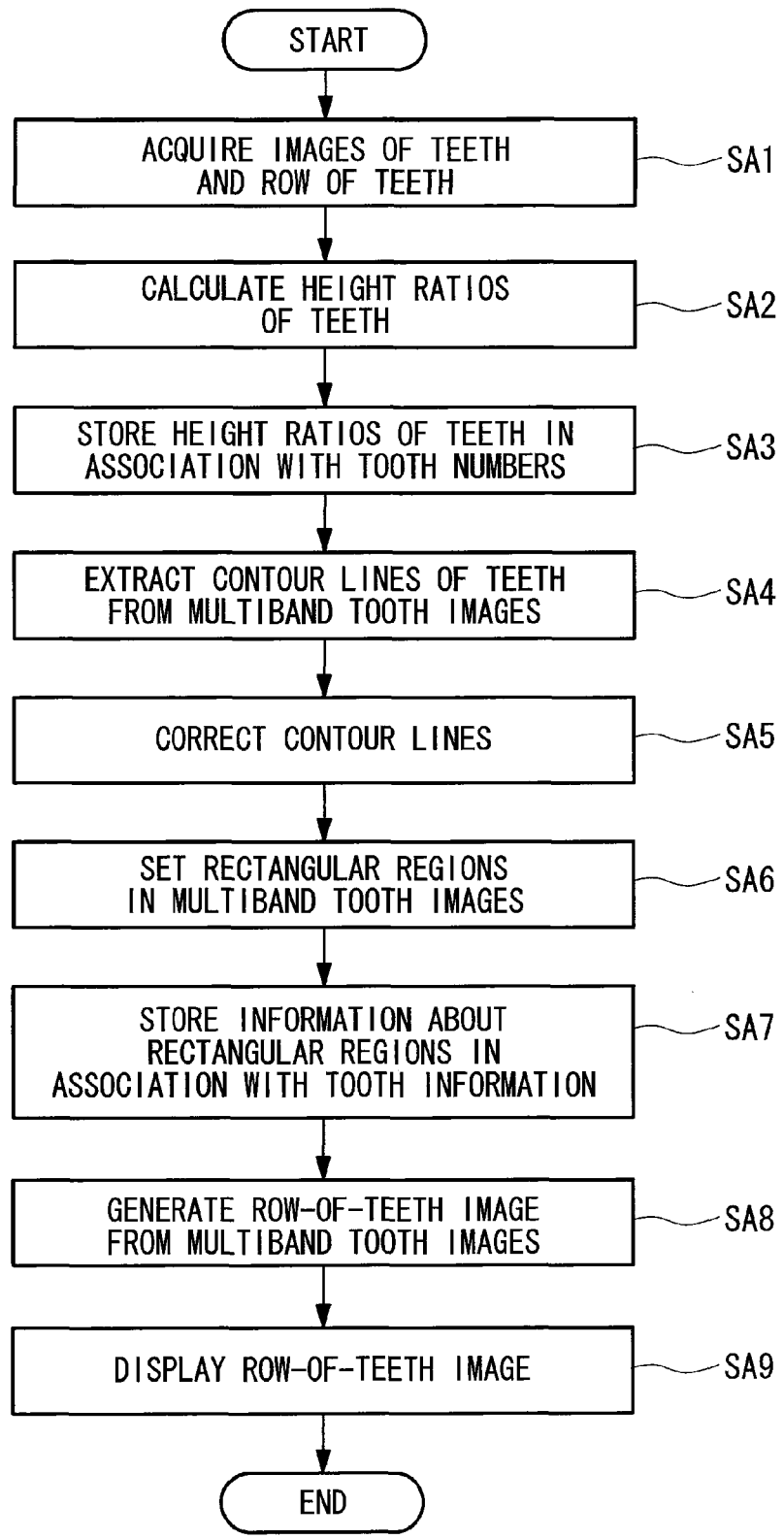
FIG. 6 is a flowchart showing processing steps in the dental colorimetry apparatus in FIG. 1.

First, the dentist acquires images of the patient's teeth using the image-acquisition device 1 (Step SA1 in FIG. 6). Specifically, the dentist acquires an image of the patient's row of teeth in the normal image acquisition mode and images of the patient's individual teeth in the multiband image acquisition mode. The images thus acquired are transmitted from the image-acquisition device 1 to the dental colorimetry apparatus 2.

In the dental colorimetry apparatus 2, the multiband images of the individual teeth are stored in the multiband-image storing section 21 in association with the tooth numbers thereof, whereas the row-of-teeth image is stored in the row-of-teeth-image storing section 22. The relative-tooth-size calculating section 23 then reads the row-of-teeth image from the row-of-teeth-image storing section 22 and uses it to calculate the height ratios of the individual teeth to the representative tooth (Step SA2). The height ratios are stored in association with the respective tooth numbers in the relative-ratio storing section 24 (Step SA3).

Next, the contour-line extracting section 25 reads the multiband images of the individual teeth stored in the multiband-image storing section 21 and extracts the contour lines of the individual teeth from the multiband images (Step SA4). The information about the extracted contour lines is output to the contour-correcting section 26. The contour-correcting section 26 then reads the height ratios of the individual teeth stored in the relative-ratio storing section 24 and corrects the contour lines based on the height ratios (Step SA5). As a result, the sizes of the teeth in the multiband images are adjusted to the height ratios of the teeth in the row-of-teeth image.

The multiband images of the teeth with the contour information corrected by the contour-correcting section 26 are output to the rectangle-setting section 27, which sets rectangular regions in the individual multiband images (Step SA6). The information about the set rectangular regions is stored in association with the tooth numbers in the rectangular-image storing section 28 (Step SA7). The image-generating section 29 then reads the multiband images of the individual teeth from the multiband-image storing section 21 and the information about the positions of the rectangular regions from the rectangular-image storing section 28 and generates a row-of-teeth image in which the multiband images of the teeth are arranged according to the respective tooth numbers so that the rectangular regions set in the multiband images adjoin each other (Step SA8). The row-of-teeth image is displayed on the display unit 15 (Step SA9). Thus, a row-of-teeth image as shown in FIG. 7 is displayed on the display unit 15.

Figure 7:
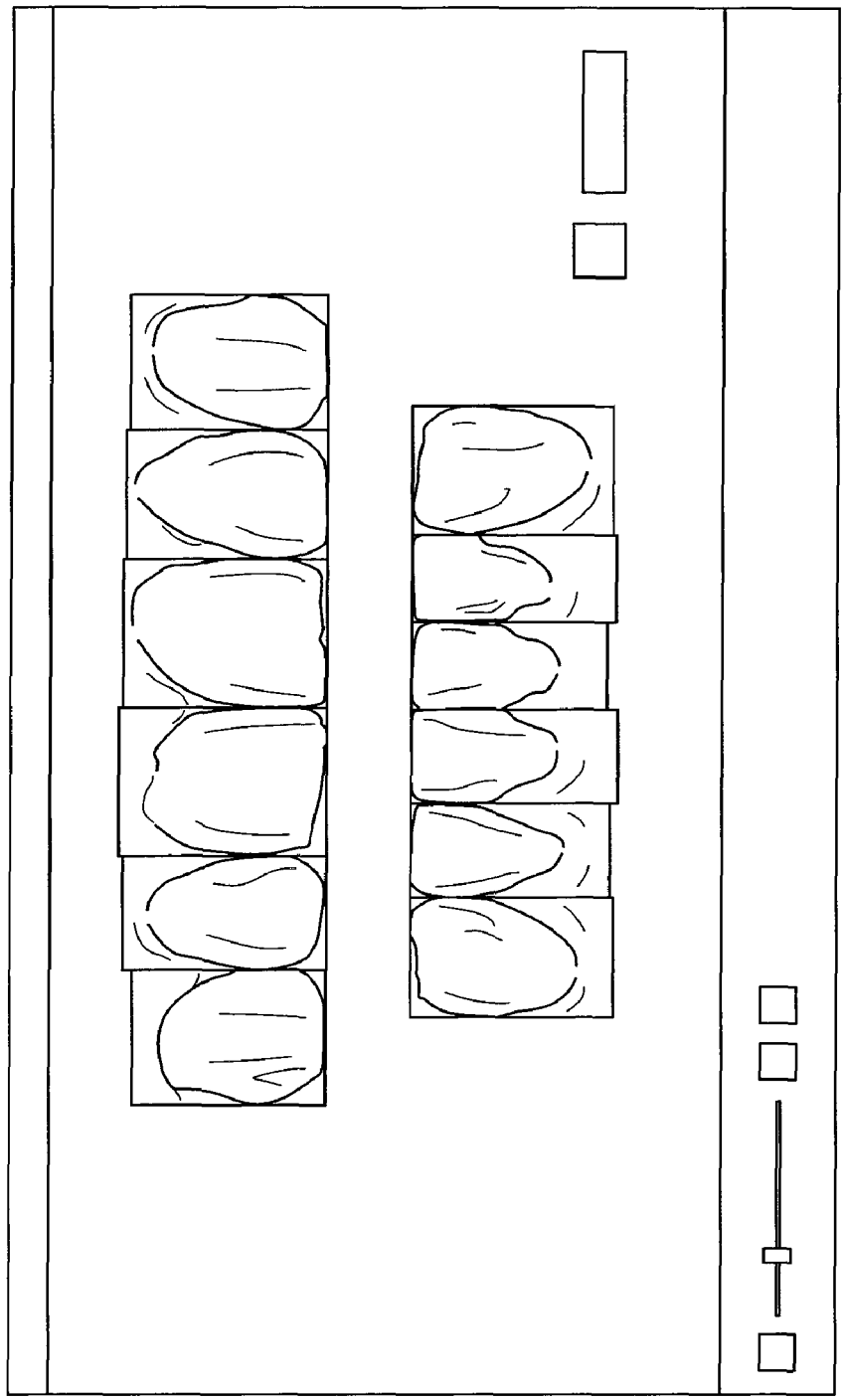
FIG. 7 is a diagram showing an example of a row-of-teeth image generated by the dental colorimetry apparatus in FIG. 1.

In the display screen shown in FIG. 7, if the user inputs the number of a certain tooth and the number of a certain shade guide via the input unit 14, the color of the designated shade guide is displayed so as to replace the color of the designated tooth. Accordingly, for example, if a dental filler such as a composite resin or a crown material such as a prosthetic is to be applied to a defective tooth, the user can check how the tooth will look in the entire row of teeth after treatment. This allows the user to select a dental filler with a more natural color.

According to this embodiment, as described above, a rectangular region is set in the multiband image of each tooth so as to include the contour line of the tooth and to circumscribe both sides of the tooth, and a row-of-teeth image is generated by arranging the multiband images of the teeth so that the rectangular regions adjoin each other. This eliminates unnecessary information about the adjacent teeth appearing in each multiband image, thus allowing only the necessary teeth to be displayed side by side.

Figure 8:
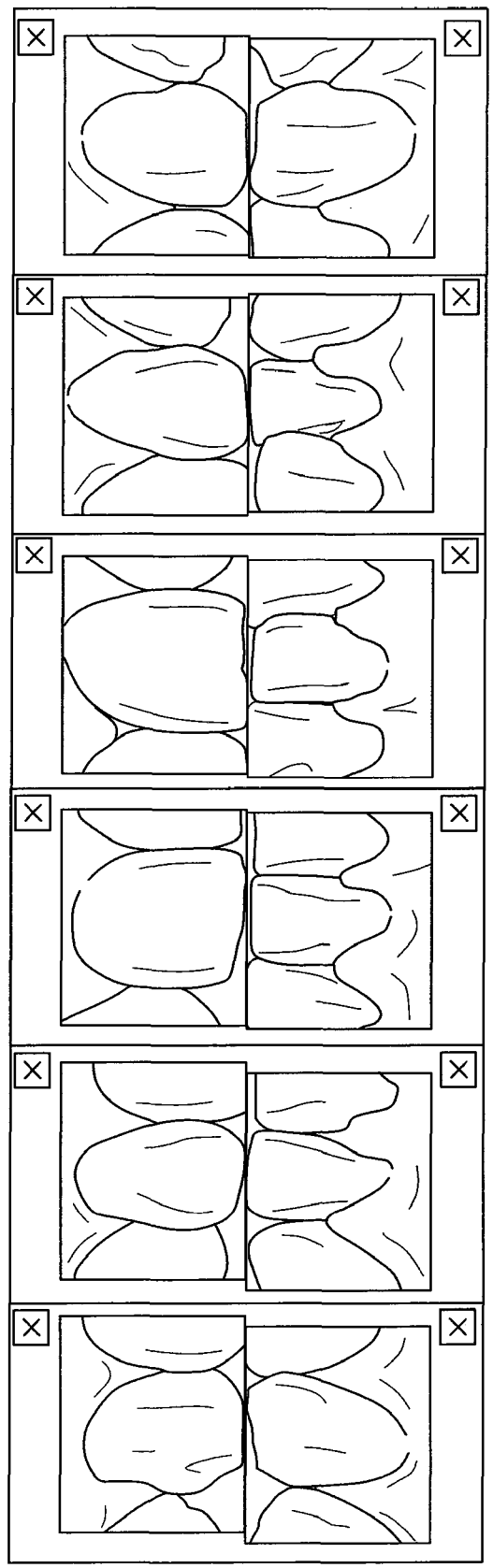
FIG. 8 is a diagram showing an example of a row-of-teeth image in which adjacent teeth appear.

As a result, a natural, easily viewable row-of-teeth image can be generated and displayed as compared with a row-of-teeth image generated by arranging multiband images in which parts of the adjacent teeth appear, for example, as shown in FIG. 8.

According to this embodiment, additionally, the color of at least one of the teeth constituting the row of teeth can be replaced with the color of a desired shade guide. Accordingly, for example, if the color of a defective tooth is to be changed after treatment, the color balance of the entire row of teeth can be checked in advance.

Although the multiband tooth images on which the rectangular regions are superimposed are displayed side by side to reproduce the row of teeth in the above embodiment, a row-of-teeth image may instead be generated by cutting the multiband tooth images themselves along the rectangular regions into rectangular multiband images and arranging the rectangular multiband images so that the sides thereof adjoin each other. This reduces the amount of image data as compared with the case where the rectangular regions are superimposed on the tooth images, as in the above embodiment.

In addition, although the row-of-teeth image of the patient is acquired and is used to determine the relative height ratios of the teeth by the relative-tooth-size calculating section 23 in the above embodiment, the relative height ratios of the teeth may instead be determined in advance from a reference row-of-teeth image and be stored in the relative-ratio storing section 24 in advance. This eliminates the need for the process to determine the relative height ratios of the teeth from an actual row-of-teeth image, thus simplifying the system configuration and reducing the number of processes.

In the above embodiment, additionally, multiband images of tooth-shaped shade guides may be acquired by the image-acquisition device 1 in advance and be stored in the shade-guide storing section 30 so that, for example, when a row-of-teeth image is generated, the user can designate whether to use the multiband images of the shade guides or the multiband images of the patient's actual teeth stored in the multiband-image storing section 21 for each tooth.

Thus, by initially using the multiband image of a shade guide for the tooth requiring treatment, a row-of-teeth image in which the tooth has been replaced with the shade guide in advance can be generated and displayed on the display unit 15.

In the above embodiment, additionally, it is possible to replace the image of a certain tooth in the row-of-teeth image with a laterally inverted image of the tooth located at the position laterally symmetrical with respect to the center (median) of the row of teeth and to display the inverted image. In this case, first, the user selects and inputs the tooth number of a certain tooth using the input unit 14, so that the number is sent to the image-generating section 29. Specifically, the user inputs the number using a keyboard, or selects the tooth in the row-of-teeth image using, for example, a mouse to input the number corresponding to the selected tooth.

Based on the tooth number, the image-generating section 29 reads the information, stored in the rectangular-image storing section 28, about the rectangular region for the tooth located at the position symmetrical to the selected tooth with respect to the center of the row of teeth and also reads the image of that tooth stored in the multiband-image storing section 21. The read tooth image is newly associated with the tooth number of the selected tooth. The image-generating section 29 then superimposes the rectangular region on the read tooth image, laterally inverts the image, and generates a row-of-teeth image again by arranging it with the images of the other teeth based on the tooth numbers. Thus, the image of the tooth located at the position symmetrical to the selected tooth is inserted so as to replace the image of the selected tooth.

In this case, even if the row of teeth include a missing tooth or a defective tooth, such as a decayed tooth, a row-of-teeth image showing how the teeth will look after treatment can be virtually displayed so that the color of the patient's row of teeth after treatment can be checked before the treatment.

In the above embodiment, as described above, the images inside the rectangular regions are displayed so as to be superimposed on the images outside the rectangular regions; instead, a row-of-teeth image similar to that shown in FIG. 7 may be obtained by preparing tooth images by cutting the multiband tooth images along the rectangular regions when they are set in the tooth images, and displaying the tooth images side by side without spaces, based on the tooth numbers thereof. Thus, if the images are cut along the rectangular regions, a row-of-teeth image can be easily generated simply by arranging the images.

In the above embodiment, additionally, if the tooth image corresponding to a particular tooth number is not present because, for example, the tooth is missing from the row of teeth, the image-generating section 29 may generate a row-of-teeth image by placing an empty image in the region corresponding to the tooth number of the missing tooth. In this case, a rectangular region with a predetermined size is set in the empty image, and the multiband tooth images corresponding to the tooth numbers of the adjacent teeth are arranged so as to adjoin this rectangular region. The size of the rectangular region may be set to any size. For example, it is possible to set a size common among all teeth, to set a statistically standard size for each tooth number, or to set the size of the rectangular region set in the image of the same patient's tooth located at the position laterally symmetrical with respect to the center of the row of teeth.

In addition, the image-generating section 29 may generate a row-of-teeth image without placing an empty image in the region corresponding to the missing tooth by arranging the tooth image of a healthy tooth adjacent to the side of the missing tooth facing away from the center of the row of teeth so that it adjoins the tooth image of a healthy tooth adjacent to the side of the missing tooth facing the center of the row of teeth. In this case, the image corresponding to the tooth number of the missing tooth is not displayed, but a row-of-teeth image in which the tooth images of the healthy teeth in the entire row of teeth are shifted to the center of the row of teeth is generated.

Next, a dental colorimetry apparatus 40, a dental colorimetry system, a dental colorimetry method, and a dental colorimetry program according to a second embodiment of the present invention will be described below with reference to the drawings.

In the description of this embodiment, the components common to the dental colorimetry apparatus 2, the dental colorimetry system, the dental colorimetry method, and the dental colorimetry program according to the first embodiment described above are denoted by the same reference numerals, and a description thereof will be omitted.

Figure 9:
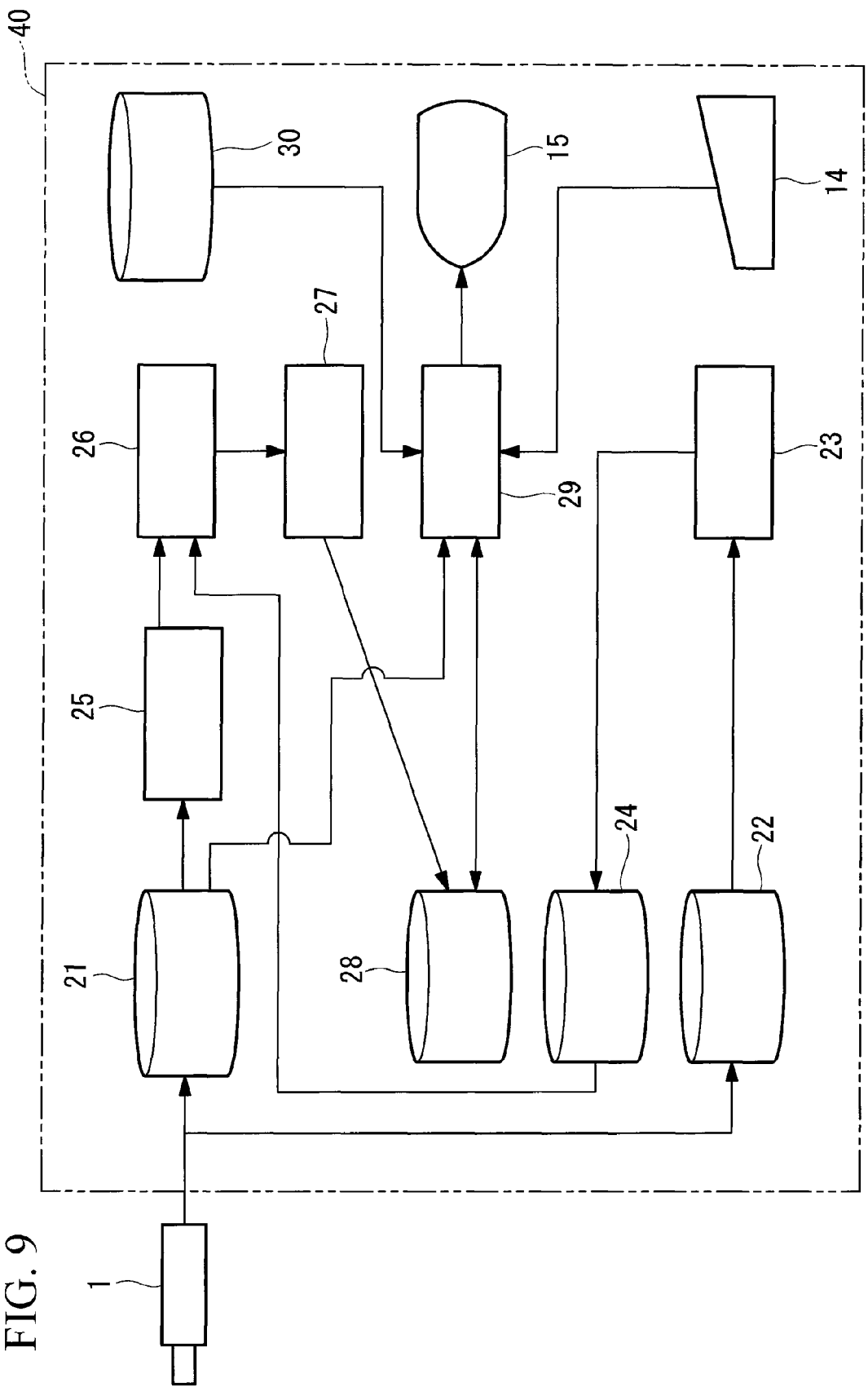
FIG. 9 is a diagram showing the overall configuration of a dental colorimetry apparatus according to a second embodiment of the present invention.

As shown in FIG. 9, the dental colorimetry apparatus 40 according to this embodiment differs from the dental colorimetry apparatus 2 according to the first embodiment in what is the input via the input unit 14, the processing in the image-generating section 29, and the information stored in the rectangular-image storing section 28.

In this embodiment, the rectangular-image storing section 28 stores tooth images in which rectangles have been set by the rectangle-setting section 27.

In the first embodiment, if a missing tooth or a defective tooth, such as a decayed tooth, is present in one of the tooth images constituting the row-of-teeth image generated by the image-generating section 29 and displayed on the display unit 15, the user may wish to display a row-of-teeth image in which the tooth appears in a healthy condition after treatment.

Figure 10:
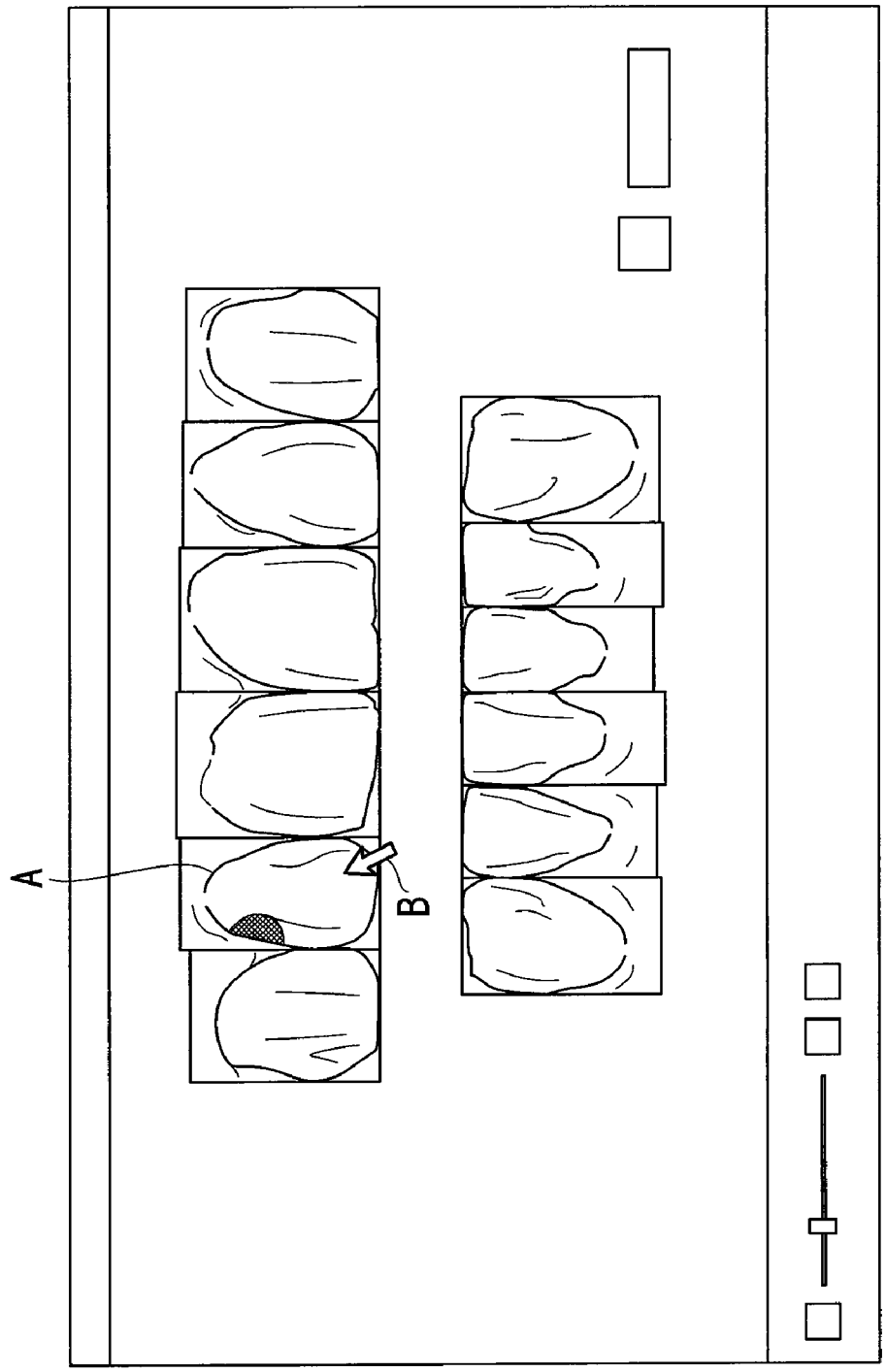
FIG. 10 is a diagram explaining a process of designating a defective tooth on a display screen using the dental colorimetry apparatus in FIG. 9.

In such a case, the user designates the defective tooth displayed on the display unit 15 by manipulating the input unit 14. In the example shown in FIG. 10, the user designates a defective tooth A in the row-of-teeth image displayed on the screen of the display unit 15 by a cursor B.

Figure 11:
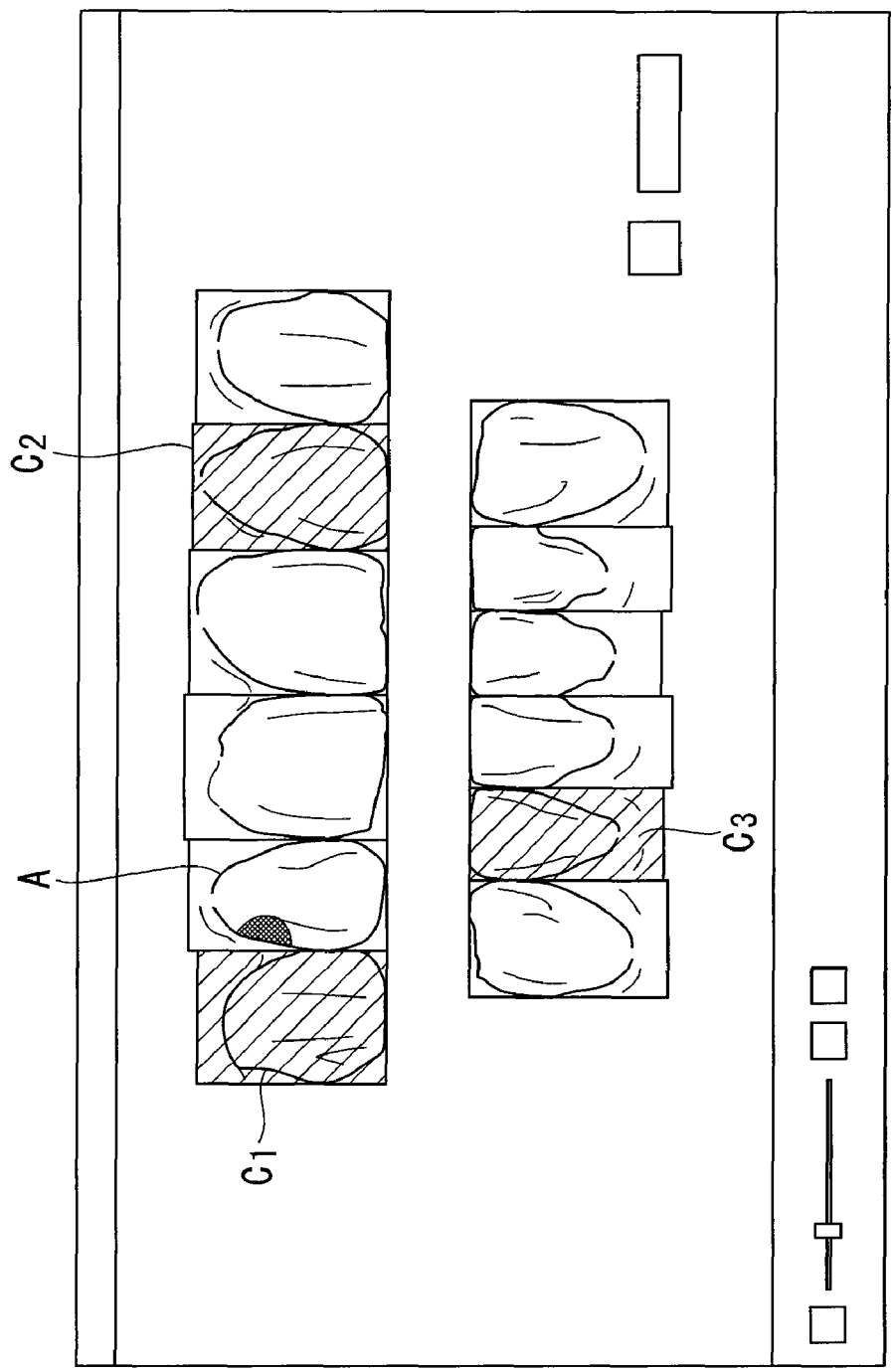
FIG. 11 is a diagram showing an example of a display screen displaying candidate healthy teeth to replace the defective tooth designated in FIG. 10.

Then, as shown in FIG. 11, one or more candidate healthy teeth C1, C2, C3 that can replace the defective tooth A are displayed (hatched teeth in the figure). When the user selects one of the candidate healthy teeth C1, C2, C3, the tooth image of the selected healthy tooth is duplicated and replaces the tooth image of the defective tooth A such that the healthy tooth lies in the same orientation as the defective tooth A.

Specifically, the candidate healthy teeth C1, C2, C3 displayed can be exemplified by a healthy tooth C1 adjacent to the defective tooth A, a healthy tooth C2 located at the position laterally symmetrical to the defective tooth A with respect to the center of the row of teeth, and a healthy tooth C3 located at the vertically symmetrical position.

Figure 12:
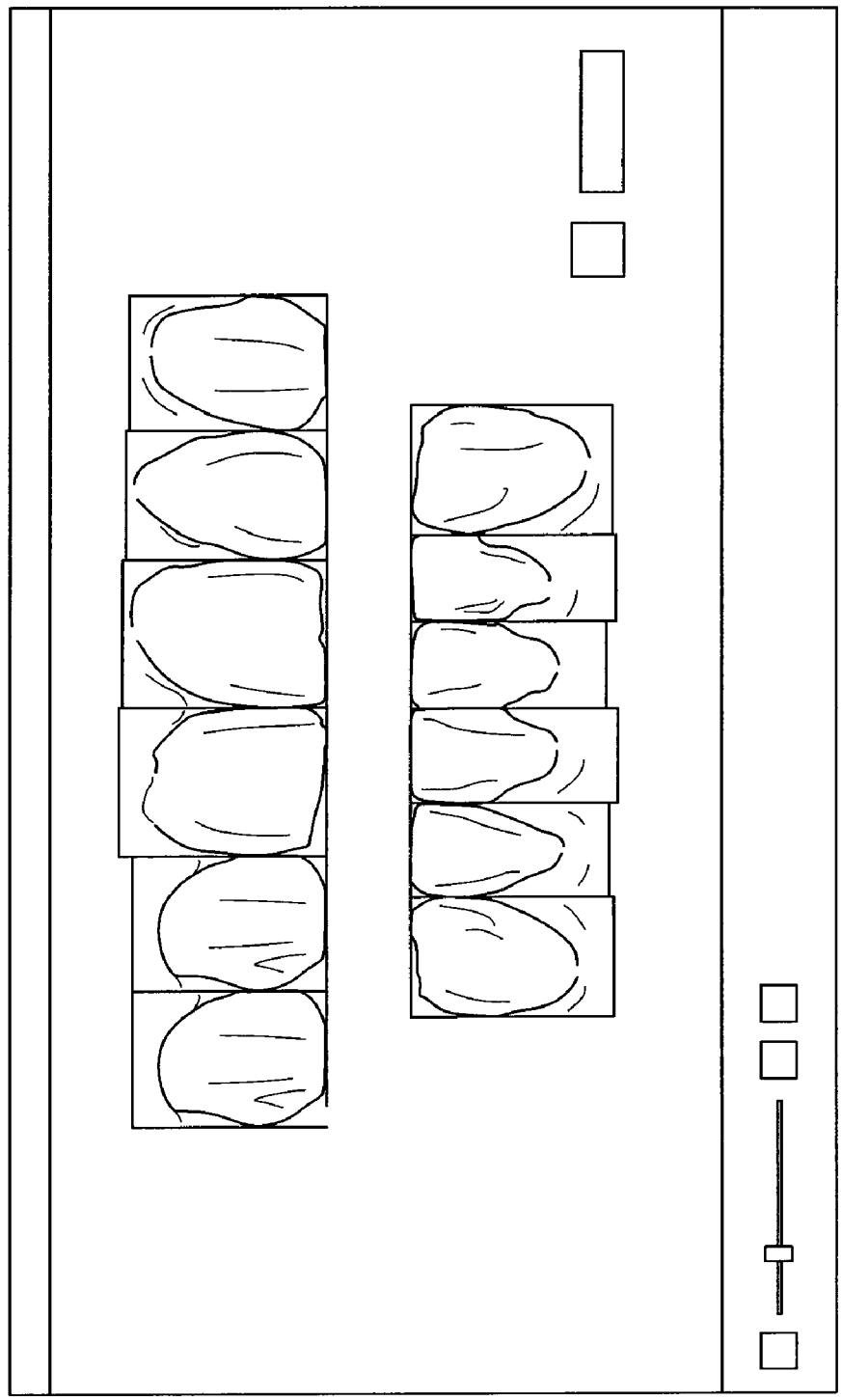
FIG. 12 is a diagram showing a row-of-teeth image in which the defective tooth designated in FIG. 10 has been replaced with a healthy tooth adjacent to the defective tooth.

If the adjacent healthy tooth C1 is selected, the image-generating section 29 duplicates the tooth image with rectangle information, stored in the rectangular-image storing section 28, corresponding to the selected healthy tooth C1 and, as shown in FIG. 12, replaces the tooth image of the designated defective tooth A with the duplicated tooth image.

Figure 13:
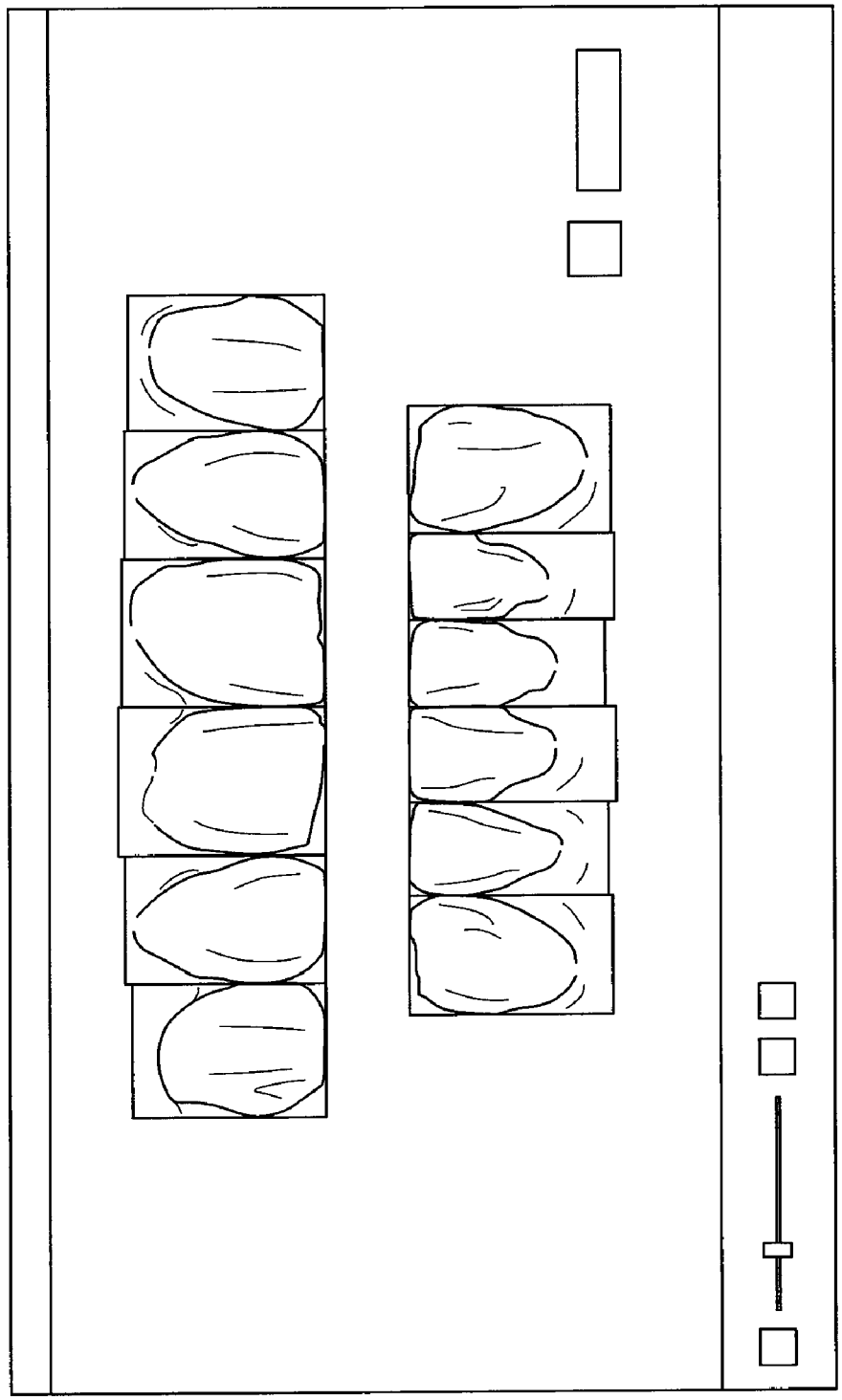
FIG. 13 is a diagram showing a row-of-teeth image in which the defective tooth designated in FIG. 10 has been replaced with a healthy tooth located at the position laterally symmetrical with respect to the center of the row of teeth.

If the healthy tooth C2 located at the position laterally symmetrical to the defective tooth A with respect to the center (median) of the row of teeth is selected, the image-generating section 29 duplicates the tooth image with rectangle information, stored in the rectangular-image storing section 28, corresponding to the selected healthy tooth C2 and, as shown in FIG. 13, replaces the tooth image of the designated defective tooth A with the duplicated tooth image such that the duplicated tooth image is laterally inverted.

Figure 14:
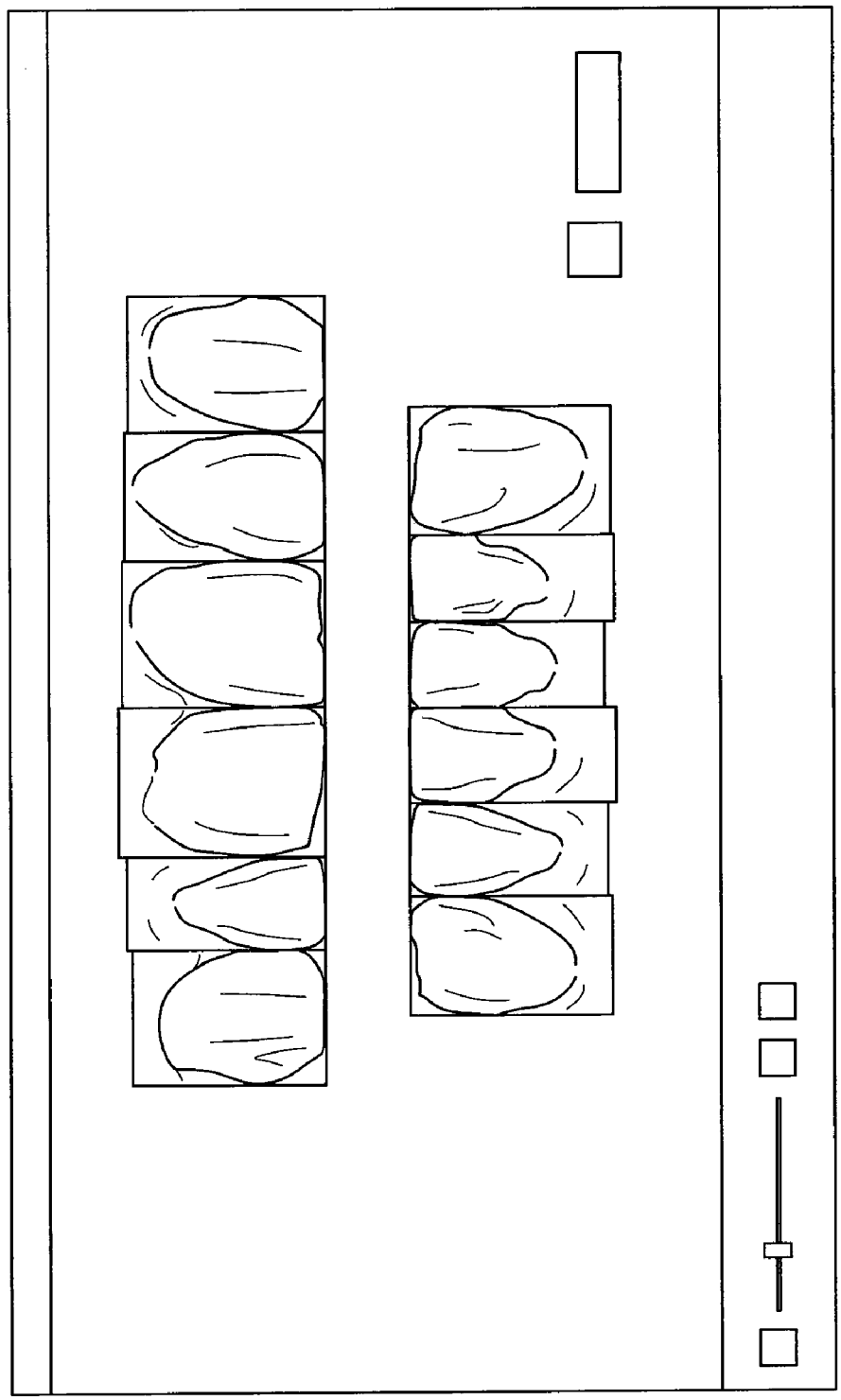
FIG. 14 is a diagram showing a row-of-teeth image in which the defective tooth designated in FIG. 10 has been replaced with a healthy tooth located at the vertically symmetrical position.

If the healthy tooth C3 located at the position vertically symmetrical to the defective tooth A is selected, the image-generating section 29 duplicates the tooth image with rectangle information, stored in the rectangular-image storing section 28, corresponding to the selected healthy tooth C3 and, as shown in FIG. 14, replaces the tooth image of the designated defective tooth A with the duplicated tooth image such that the duplicated tooth image is vertically inverted. If the selected healthy tooth C3 differs in size from the designated defective tooth A, the image-generating section 29 reads the rectangle information of the defective tooth A from the rectangular-image storing section 28, and vertically inverts and vertically and laterally scales up or down the tooth image of the healthy tooth C3 so that the healthy tooth C3 is inscribed in the rectangle of the defective tooth A.

In such cases, the tooth image of the selected healthy tooth C1, C2, or C3 is duplicated together with the rectangle set therein and replaces the tooth image with rectangle information of the designated defective tooth A. The image-generating section 29 then arranges the tooth images so that the rectangle set in the newly replaced tooth image adjoins the adjacent ones, thus generating a row-of-teeth image.

Thus, according to this embodiment, even if a missing tooth or a defective tooth is present at any position in the patient's row of teeth, a virtual row-of-teeth image in which a healthy tooth is added to the position of that tooth can be generated. The virtual row-of-teeth image thus generated has the advantage that the patient and the user can easily imagine how the row of teeth will look after treatment by viewing the virtual row-of-teeth image.

Although the rectangular-image storing section 28 stores the tooth images with the rectangles set therein by the rectangle-setting section 27 in this embodiment, it may instead store information about the positions of the rectangular regions that indicates where the rectangles are set in the tooth images, as in the first embodiment. In this case, the tooth image of the selected healthy tooth may be duplicated by the image-generating section 29 and be stored in the multiband-image storing section 21 as the tooth image located at the position corresponding to the defective tooth. At the same time, the rectangular region, stored in the rectangular-image storing section 28, corresponding to the tooth image of the selected healthy tooth may be duplicated and stored in the rectangular-image storing section 28.

In this embodiment, not only in the case where the healthy tooth C3 located at the position vertically symmetrical to the defective tooth A is selected, but also in the case where the healthy tooth C1 or C2 is selected, if the selected healthy tooth differs in size from the designated defective tooth A, the image-generating section 29 may scale up or down the healthy tooth so as to be inscribed in the rectangle of the defective tooth A. In this case, the tooth image of the healthy tooth C1 or C2 may be scaled up or down vertically and laterally at different ratios. This allows a row-of-teeth image naturally showing the row of teeth to be generated and displayed even if the tooth image of the defective tooth A is replaced with a healthy tooth different in size from the defective tooth A.

Although the defective tooth A is designated before the healthy tooth C1, C2, C3 to replace the defective tooth A is selected from the displayed candidate healthy teeth C1, C2, and C3 in this embodiment, the healthy tooth C1, C2, or C3 may be initially selected before the defective tooth A is designated.

In addition, if a missing tooth is present in the row of teeth, rather than a defective tooth such as a decayed tooth, the healthy tooth C1, C2, or C3 may be displayed so as to replace the missing tooth as in the above manner. In this case, the tooth image of the healthy tooth C1, C2, or C3 to replace the missing tooth may be scaled up or down so that the size of the rectangular region thereof agrees with, for example, a size common among all teeth, a statistically standard size for each tooth number, or the size of the rectangular region set in the image of the same patient's tooth located at the position laterally symmetrical with respect to the center of the row of teeth.

Next, a dental colorimetry apparatus 50, a dental colorimetry system, a dental colorimetry method, and a dental colorimetry program according to a third embodiment of the present invention will be described below with reference to the drawings.

In the description of this embodiment, the components common to the dental colorimetry apparatus 2, the dental colorimetry system, the dental colorimetry method, and the dental colorimetry program according to the first embodiment described above are denoted by the same reference numerals, and a description thereof will be omitted.

Figure 15:
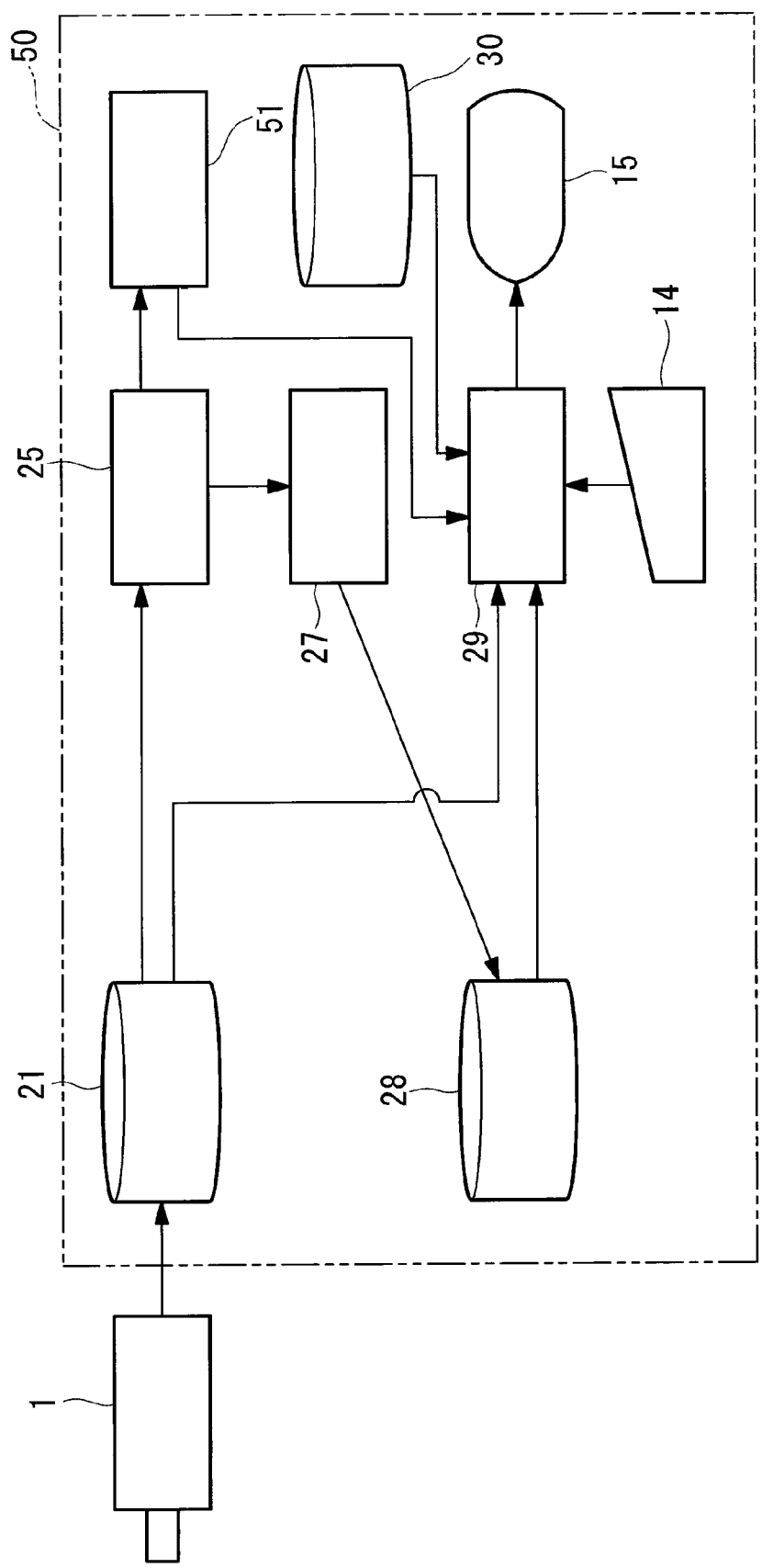
FIG. 15 is a diagram showing the overall configuration of a dental colorimetry apparatus according to a third embodiment of the present invention.

As shown in FIG. 15, the dental colorimetry apparatus 50 according to this embodiment differs from the dental colorimetry apparatus 2, the dental colorimetry system, the dental colorimetry method, and the dental colorimetry program according to the first embodiment in the processing in the contour-line extracting section 25, in that the dental colorimetry apparatus 50 excludes the row-of-teeth-image storing section 22, the relative-tooth-size calculating section 23, the relative-ratio storing section 24, and the contour-correcting section 26 and includes a contour-line-positional-relationship storing section 51, as well as in the processing in the image-generating section 29.

Figure 16:
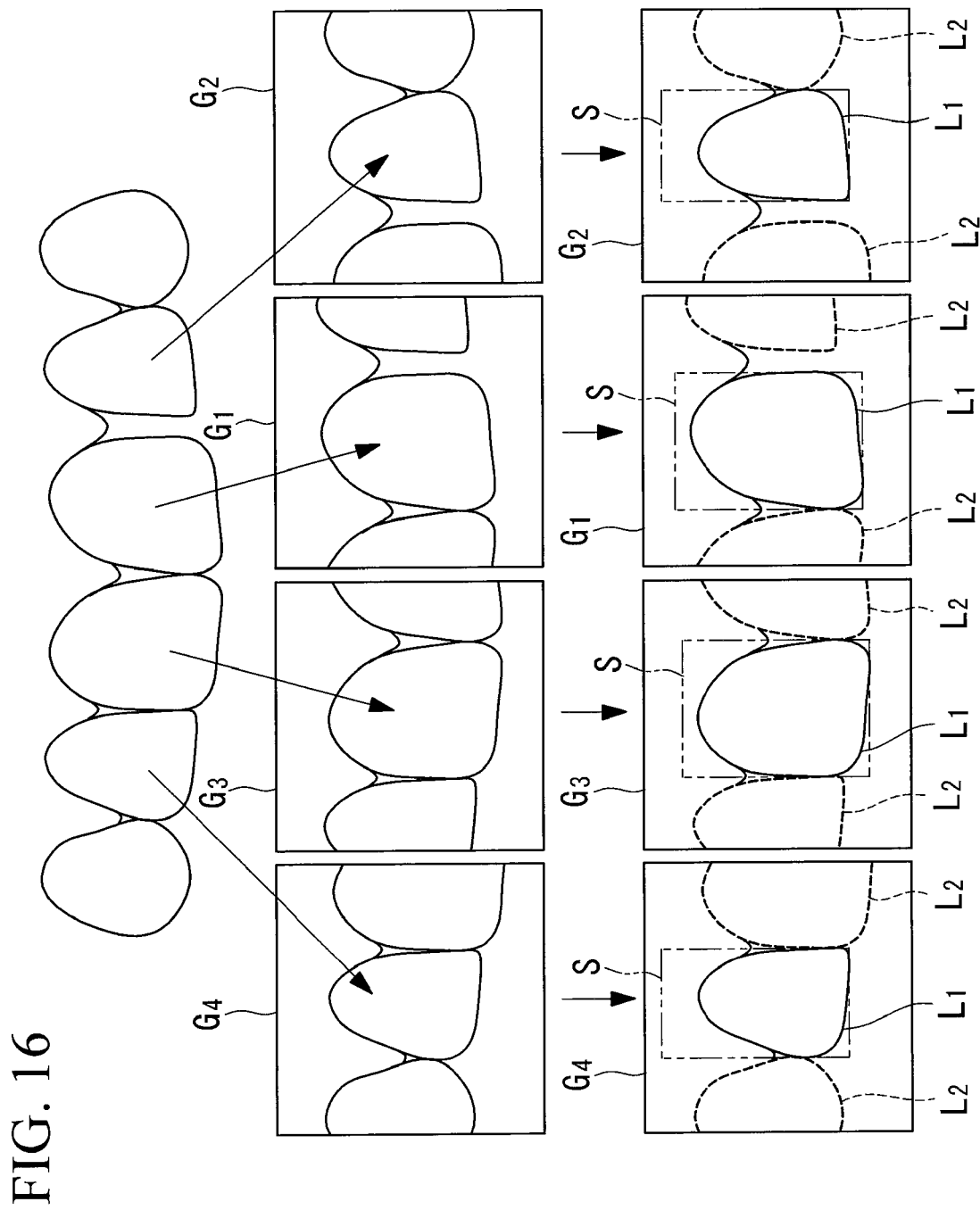
FIG. 16 is a diagram showing a row-of-teeth image acquired by the dental colorimetry apparatus of FIG. 15, tooth images clipped from the row-of-teeth image, and rectangular regions set in the tooth images.

In this embodiment, as in the first embodiment, the contour-line extracting section 25 extracts the contour lines of the images contained in the tooth images. Here, in this embodiment, the patient's actual teeth, as shown in the top of FIG. 16, are each subjected to multiband image acquisition to acquire tooth images G1 to G4, as shown in the middle of FIG. 16, each containing a central tooth (target tooth) and partial teeth (adjacent teeth) adjacent to both sides thereof. As shown in the bottom of FIG. 16, the contour-line extracting section 25 extracts the contour lines L1 of the images of the target teeth in the tooth images G1 to G4 and also extracts the contour lines L2 of the teeth adjacent thereto (adjacent teeth) partially contained in the tooth images G1 to G4.

The adjacent-positional-relationship storing section 51 stores the extracted contour lines L1 and L2 as relative position information (for example, as vector data or coordinate data) indicating the positional relationship of the contour lines L2 of the adjacent teeth relative to the contour lines L1 of the target teeth. As shown in the bottom of FIG. 16, of the teeth contained in the tooth images, the rectangle-setting section 27 sets rectangles S including the contour lines L1 of the target teeth and circumscribing at least both sides of the target teeth. In the bottom of FIG. 16, the rectangles S are set so as to circumscribe the ends of the target teeth as well.

Figure 17A:
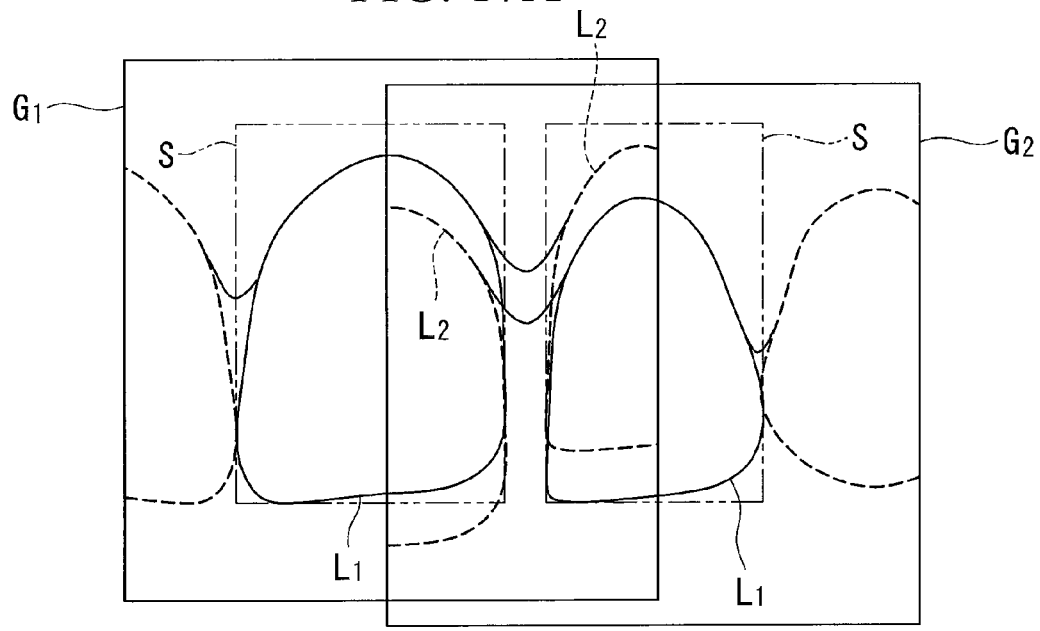
FIG. 17A is a diagram showing a method for arranging the tooth images clipped in FIG. 16.
Figure 17B:
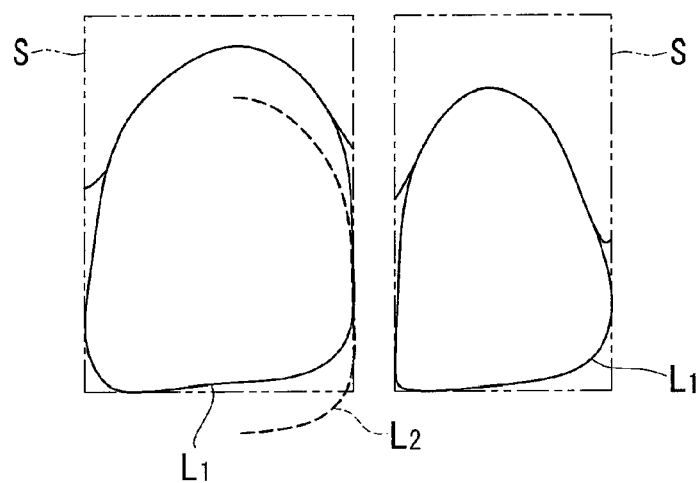
FIG. 17B is a diagram showing images inside two rectangular regions arranged by the method in FIG. 17A.

As shown in FIGS. 17A and 17B, the image-generating section 29 arranges the two tooth images G1 and G2, for example, so that the extracted contour line L2 of one of the adjacent teeth in the tooth image G2 is substantially inscribed in the rectangle S set in the tooth image G1 by the rectangle-setting section 27. In the example shown in FIGS. 17A and 17B, additionally, the two tooth images G1 and G2 are arranged so that the ends of the target teeth are located on a straight line.

Figure 17C:
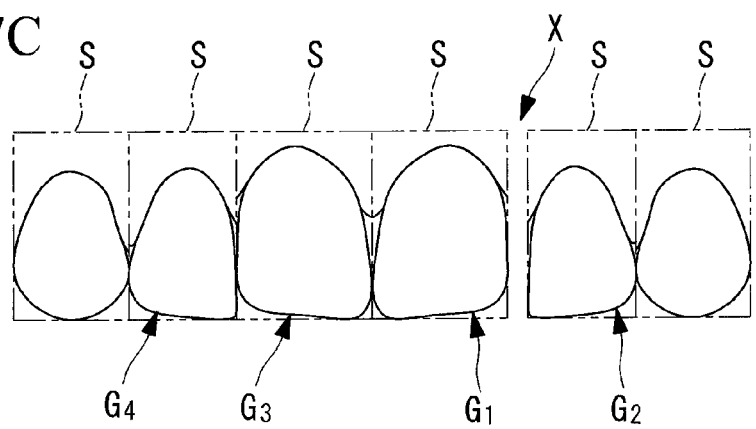
FIG. 17C is a diagram showing a row-of-teeth image generated by arranging images inside rectangular regions.

With this configuration, as shown in FIG. 17C, an advantage is provided in that, even if a gap X is present between any teeth constituting the row of teeth, a row-of-teeth image close to the patient's actual tooth arrangement, including the gap X, can be generated.

That is, some patients have the gap X between any teeth constituting the row of teeth, and the gap X between the teeth disappears if the tooth images G1 to G4 are arranged so that the rectangles S adjacent to both sides of the target teeth adjoin each other, as in the first embodiment.

In contrast, in the row-of-teeth image generated in this embodiment, for example, the distance between the contour line L1 of the target tooth in the tooth image G1 and the contour line L1 of the target tooth in the tooth image G2 adjacent thereto substantially agrees with the distance between the contour line L1 of the target tooth and the contour line L2 of one of the adjacent teeth in the tooth image G1 or the tooth image G2 adjacent thereto.

Accordingly, if the gap X is present between the teeth or, conversely, some adjacent teeth overlap each other, a row-of-teeth image in which the gap X or the overlap is reproduced can be generated. Thus, a row-of-teeth image close to the patient's actual tooth arrangement can be generated so that proper calorimetric analysis can be performed in a row-of-teeth state close to the actual state.

Figure 18A:
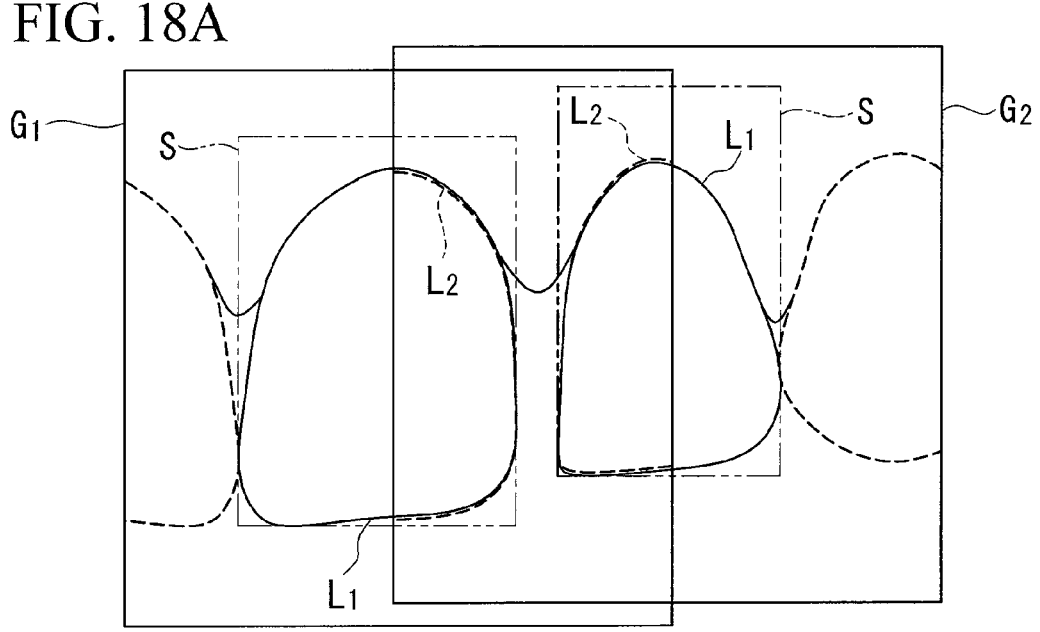
FIG. 18A is a diagram showing a modification of the method in FIG. 17A for arranging the tooth images clipped in FIG. 16.
Figure 18B:
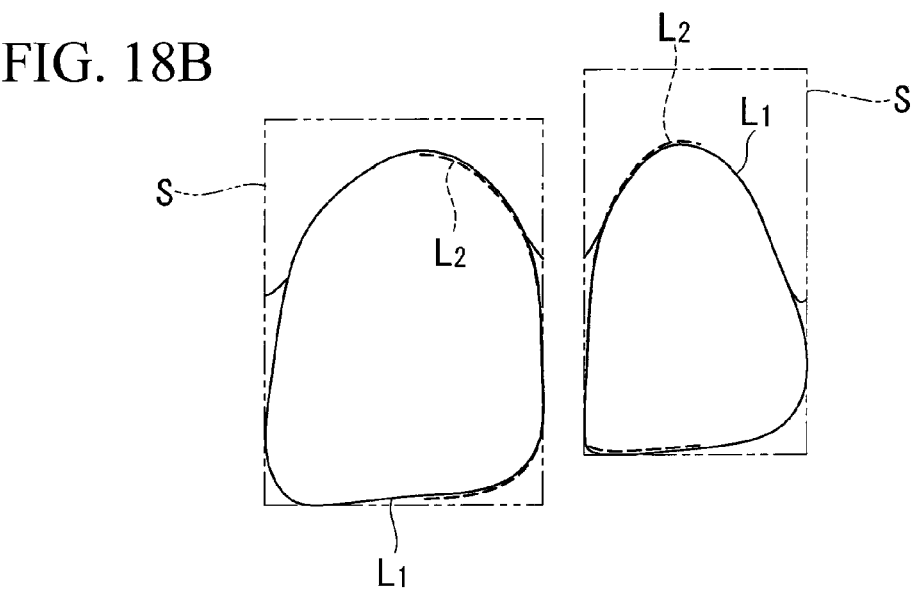
FIG. 18B is a diagram showing images inside two rectangular regions arranged by the method in FIG. 18A.
Figure 18C:
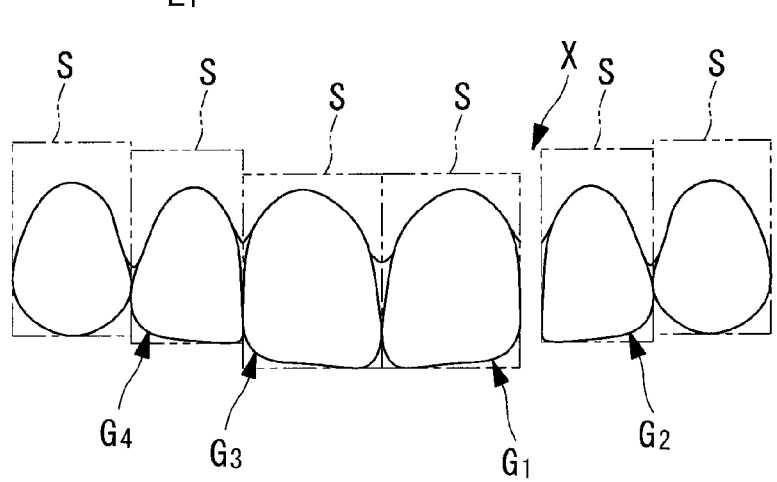
FIG. 18C is a diagram showing a row-of-teeth image generated by arranging images inside rectangular regions.

In this embodiment, additionally, as shown in FIGS. 18A and 18B, the image-generating section 29 may adjust the positions of, for example, the two tooth images G1 and G2 so that the contour line L1 of the target tooth in the tooth image G1 substantially coincides with the contour line L2 of one of the adjacent teeth in the adjacent tooth image G2. That is, the positions of the teeth in the height direction are not adjusted to those in the patient's actual tooth arrangement if the contour line L2 of one of the adjacent teeth in the adjacent tooth image G2 is simply inscribed in the rectangle S of the target tooth in the tooth image G1; the positions of the teeth in the height direction can be adjusted if the contour line L1 of the target tooth in the tooth image G1 substantially coincides with the contour line L2 of one of the adjacent teeth in the adjacent tooth image G2. As shown in FIG. 18C, this provides the advantage that a row-of-teeth image closer to the patient's actual tooth arrangement (see the top of FIG. 16) can be generated.

An example of a method for making the contour lines L1 and L2 substantially coincide with each other is to relatively move the tooth images G1 and G2 to search for the position where the mismatch between the contour lines L1 and L2 is minimized.

Although the individual tooth images G1 to G4 are acquired right in front of the target teeth in the tooth images G1 to G4, the angle of image acquisition differs between the tooth images G1 to G4 because the patient's actual row of teeth have an arch shape that curves backward in the row-of-teeth direction.

Hence, the contour line L1 of the target tooth in the tooth image G1 does not completely coincide with the contour line L2 of one of the adjacent teeth in the adjacent tooth image G2. Accordingly, the positions of the two tooth images G1 and G2 can be adjusted by searching for the position where the mismatch is minimized or becomes lower than a predetermined threshold, rather than searching for the position where the mismatch becomes zero.

Figure 19A:
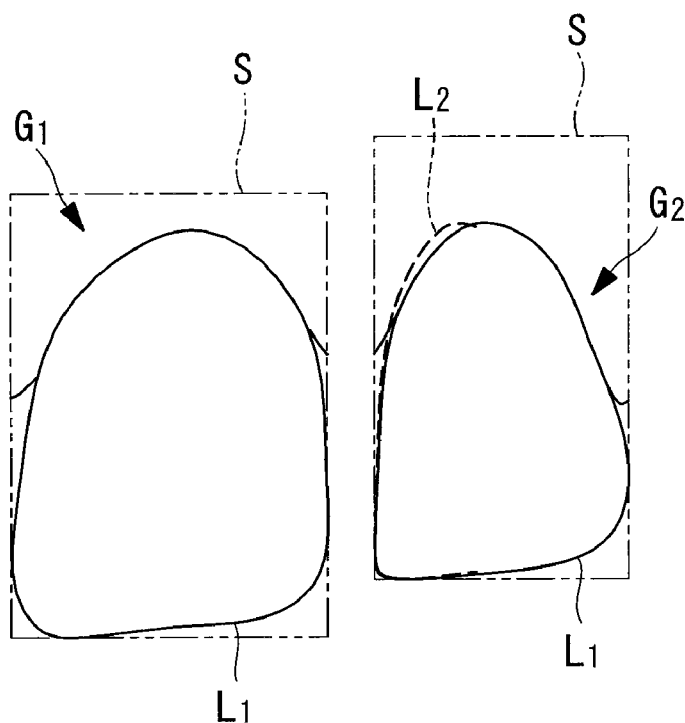
FIG. 19A is a diagram of another modification of the method in FIG. 17A, showing images inside two arranged rectangular regions before the arch structure of the row of teeth is taken into account.

In addition, because the angle of image acquisition differs between the individual tooth images depending on the arch shape of the row of teeth, as shown in FIG. 19A, the curvature of the contour line L1 of the target tooth in the tooth image G1 may differ from that of the contour line L2 of one of the adjacent teeth in the adjacent tooth image G2.

For example, as the actual row of teeth are viewed with respect to the center of the row of teeth, the teeth turn increasingly sideways the farther they are from the center towards both ends of the row of teeth; therefore, the curvatures of the sides of the teeth become smaller the farther the are from the center towards both ends.

Figure 19B:
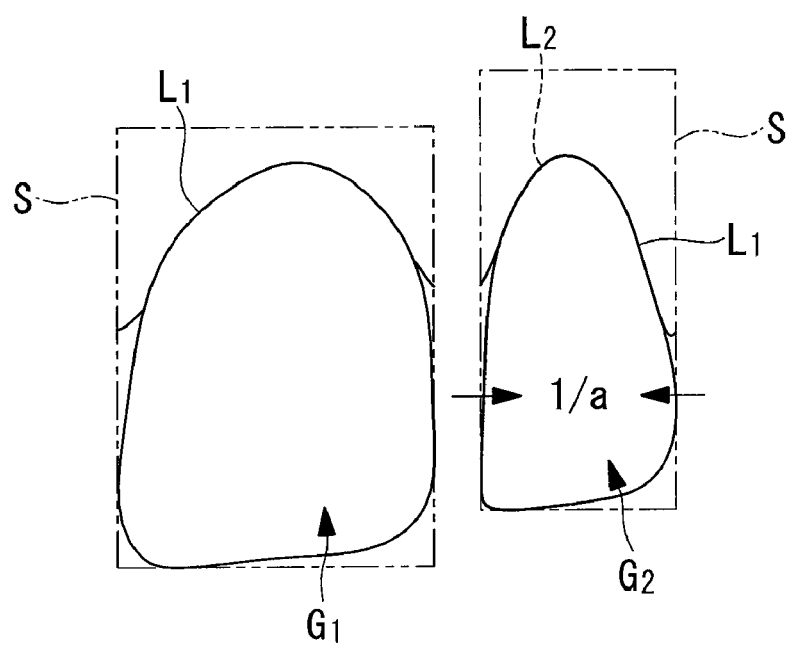
FIG. 19B is a diagram of the modification of the method in FIG. 17A, showing the images inside the two arranged rectangular regions after the arch structure of the row of teeth has been taken into account.

Accordingly, to arrange the tooth image G1 closer to the center of the row of teeth and the tooth image G2 adjacent thereto in the direction away from the center, as shown in FIG. 19B, the side curvature of the contour line L1 of the target tooth in the tooth image G2 adjacent thereto in the direction away from the center may be reduced by scaling down the tooth image G2 in the row-of-teeth direction so that the contour line L1 is closer in curvature to the contour line L2 of one of the adjacent teeth in the tooth image G1 closer to the center.

Figure 20A:
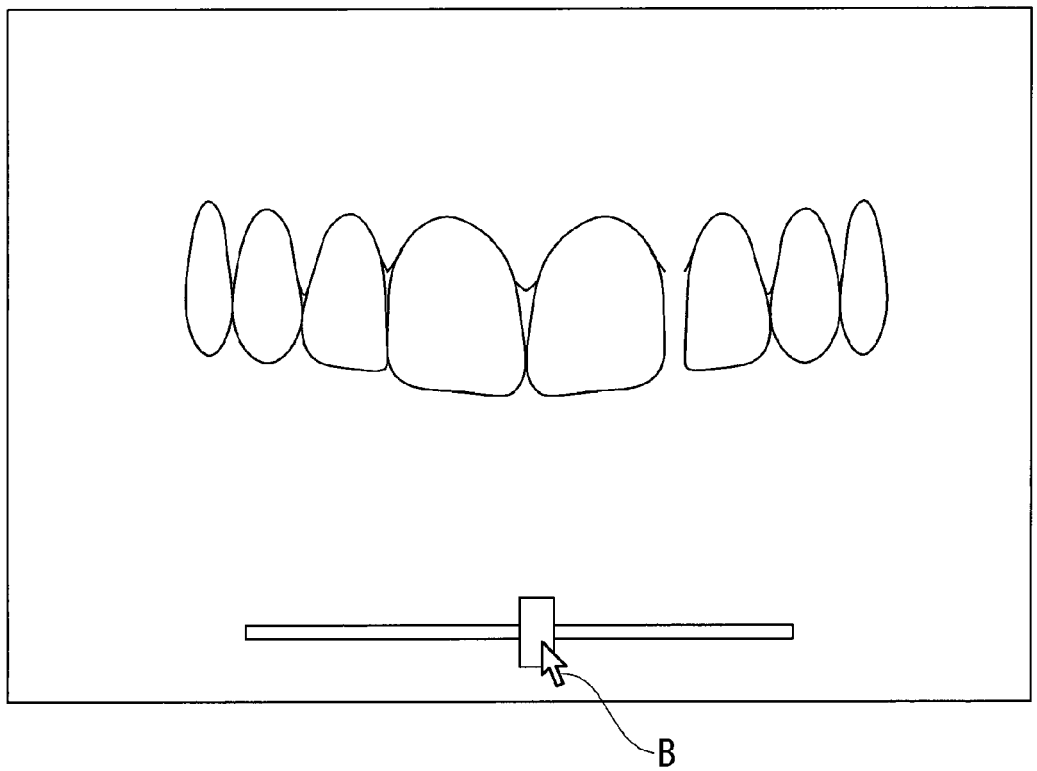
FIG. 20A is a diagram, as viewed from the front of the row of teeth, showing a viewpoint position displayed on a display screen and explaining the operation thereof.

By doing so, as shown in FIG. 20A, a row-of-teeth image is generated in which the teeth located farther away from the center in the row-of-teeth direction have smaller lateral widths. Thus, a backward arching shape can be represented. Accordingly, a row-of-teeth image close to the actual tooth arrangement can be displayed.

Figure 20B:
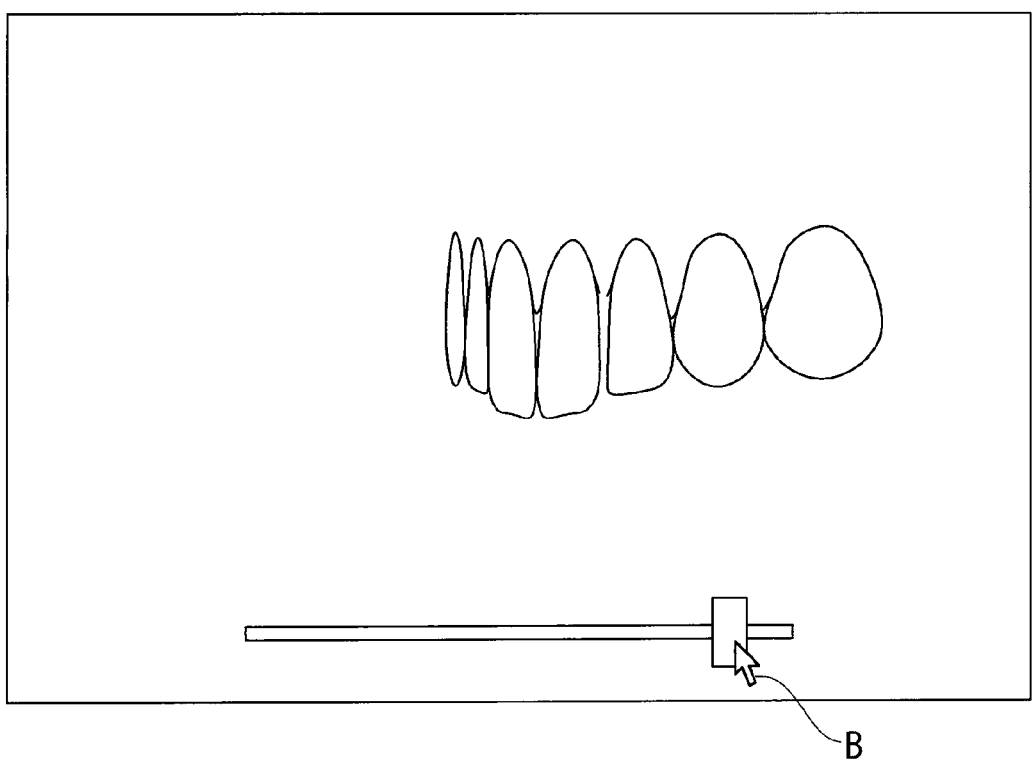
FIG. 20B is a diagram, as viewed from the side of the row of teeth, showing the viewpoint position displayed on the display screen and explaining the operation thereof.

In this case, additionally, as shown in FIGS. 20A and 20B, it is preferable to display the viewpoint position on the display screen so that the position can be changed. In the example shown in FIGS. 20A and 20B, the viewpoint position is represented by the horizontal position of a slider over a slide bar and can be changed by moving the slider horizontally using a cursor B.

In this case, a backward arching shape can be represented by changing the scale-down ratio of each tooth in the row-of-teeth direction depending on the viewpoint, specifically, by displaying the teeth located farther away from the viewpoint in the row-of-teeth direction at larger scale-down ratios, with the magnification being 1 at the viewpoint position, either as viewed from the front of the row of teeth, as shown in FIG. 20A, or as viewed in the lateral direction of the row of teeth, as shown in FIG. 20B.

In the above embodiments, based on the generated row-of-teeth image, it is possible to execute a shade-guide selection process for selection of the shade guide closest to the measurement region serving as the target in the row of teeth and to display the selected shade guide on the display unit 15. The shade-guide selection process may be implemented by various methods.

For example, it is possible to employ a method in which, for example, the colorimetry values, such as XYZ tristimulus values or chromaticity values, or a reflectance spectrum, obtained based on the multiband tooth images, of the measurement region in the row of teeth are compared with those of the individual shade guides to determine the shade guide with the smallest difference from the measurement region. It is also possible to employ a method in which the multiband tooth images are subjected to discrimination arithmetic using a discrimination function, as disclosed in Japanese Unexamined Patent Application, Publication No. HEI-7-120324, to obtain class data for shade guides.

In this case, the measurement region serving as the target may be a region corresponding to part of a single tooth or a plurality of regions on a plurality of teeth. For a plurality of measurement regions, preferably, a plurality of selected shade guides are displayed at positions adjacent to the row-of-teeth image in association with the respective measurement regions.

It is also possible to divide the generated row-of-teeth image into a plurality of regions, each of which is defined by a plurality of pixels, and to display the labels of the shade guides closest to the individual regions or to perform color mapping by putting different pseudocolors in the individual regions.

In addition, it is possible to select, for example, any color of shade guides or color chart etc. as a reference color to perform color correction on the entire row-of-teeth image or the tooth regions so that the reference color replaces the color of the region serving as the target in the row of teeth. This enables color simulation on the row-of-teeth image.

What is claimed is:

1. A dental colorimetry apparatus comprising:
a first storage section storing a plurality of images of a plurality of teeth constituting a row of the teeth in association with information about the positions of the teeth in the row of the teeth, respectively;
a contour-line extracting section for extracting contour lines of the teeth from the plurality of images of the plurality of teeth, respectively;
a rectangle-setting section for setting rectangles in the images of the plurality of teeth so as to include the contour lines extracted by the contour-line extracting section and so as to circumscribe at least both sides of the teeth, respectively; and
an image-generating section for generating a row-of-teeth image by arranging the images of the plurality of teeth based on the information about the positions of the plurality of teeth in the row of the teeth so that the rectangles adjoin each other.

2. The dental colorimetry apparatus according to claim 1, wherein:
the rectangle-setting section sets the rectangles so as to include the contour lines and so as to circumscribe at least both sides and ends of the teeth; and
the image-generating section generates the row-of-teeth image by arranging the images of the teeth so that edges, adjoining the ends of the teeth, of the rectangles are located at a same height.

3. The dental colorimetry apparatus according to claim 1, wherein:
the rectangle-setting section sets the rectangles so as to circumscribe ends of the teeth; and
the image-generating section arranges the images of the teeth so that edges, adjoining the ends of the teeth, of the rectangles are located farther away from a centerline between top and bottom rows of teeth in directions away from a center of the row of teeth along the row of teeth.

4. The dental colorimetry apparatus according to claim 1, further comprising:
a second storage section storing information about relative sizes of the teeth determined from a reference row-of-teeth image; and
a contour-correcting section for correcting the contour lines of the teeth based on the information about the relative sizes of the teeth stored in the second storage section.

5. The dental colorimetry apparatus according to claim 4, wherein the images of the teeth stored in the first storage section and the reference row-of-teeth image are acquired from a same patient.

6. The dental colorimetry apparatus according to claim 4, wherein the rectangle-setting section sets the rectangles using the contour lines corrected by the contour-correcting section.

7. The dental colorimetry apparatus according to claim 1, further comprising a third storage section storing a plurality of pieces of color information,
wherein, if one of the pieces of color information stored in the third storage section is designated and at least one of the images of the teeth constituting the row-of-teeth image is designated, the designated piece of color information replaces the color of the tooth in the designated image of the tooth.

8. The dental colorimetry apparatus according to claim 1, further comprising:
an image-selecting section for selecting one of the images of the teeth stored in the first storage section;
an image-duplicating section for duplicating the image of the tooth selected by the image-selecting section; and
an image-updating section for storing the image of the tooth duplicated by the image-duplicating section in the first storage section as a tooth image having different positional information.

9. The dental colorimetry apparatus according to claim 1, further comprising:
a rectangular-image storing section storing the images of the teeth in which the rectangles are set by the rectangle-setting section in association with the information about the positions of the teeth in the row of teeth;
an image-selecting section for selecting one of the images of the teeth stored in the rectangular-image storing section;
an image-duplicating section for duplicating the image of the tooth selected by the image-selecting section; and
an image-updating section for storing the image of the tooth duplicated by the image-duplicating section in the rectangular-image storing section as a tooth image having different positional information.

10. The dental colorimetry apparatus according to claim 8, wherein the image-duplicating section duplicates the image of the tooth selected by the image-selecting section so as to be vertically or laterally inverted.

11. A dental colorimetry apparatus comprising:
a first storage section storing a plurality of tooth images containing a plurality of target teeth constituting a row of the teeth and partial adjacent teeth adjacent to the target teeth in association with information about the positions of the plurality of target teeth in the row of the teeth, respectively;
a contour-line extracting section for extracting contour lines of the plurality of target teeth and the adjacent teeth, respectively, from the plurality of tooth images;
a rectangle-setting section for setting rectangles in the plurality of tooth images so as to include the contour lines of the plurality of target teeth extracted by the contour-line extracting section and so as to circumscribe at least both sides of the target teeth, respectively; and
an image-generating section for generating a row-of-teeth image by arranging portions of the plurality of tooth images inside the rectangles based on the information about the positions of the plurality of target teeth in the row of the teeth so that the rectangles inscribe the contour lines of the adjacent teeth in the adjacent tooth images.

12. The dental colorimetry apparatus according to claim 11, wherein the image-generating section arranges the tooth images so that the contour lines of the adjacent teeth in the tooth images substantially coincide with the contour lines of the target teeth in the adjacent tooth images.

13. The dental colorimetry apparatus according to claim 11, wherein the image-generating section scales down the tooth images in a direction along the row of teeth so that the contour lines of the target teeth in the tooth images substantially coincide with the contour lines of the adjacent teeth in the adjacent tooth images.

14. A dental colorimetry system comprising:
an image-acquisition device for acquiring an image inside an oral cavity; and
a dental colorimetry apparatus for processing the image acquired by the image-acquisition device;
wherein the dental colorimetry apparatus comprises:
a first storage section storing a plurality of acquired images of a plurality of teeth constituting a row of the teeth in association with information about the positions of the plurality of teeth in the row of the teeth, respectively;
a contour-line extracting section for extracting contour lines of the teeth from the plurality of acquired images of the plurality of teeth;
a rectangle-setting section for setting rectangles in the plurality of acquired images of the plurality of teeth so as to include the contour lines extracted by the contour-line extracting section and so as to circumscribe at least both sides of the teeth, respectively;
an image-generating section for generating a row-of-teeth image by arranging the acquired images of the plurality of teeth based on the information about the positions of the plurality of teeth in the row of the teeth so that the rectangles adjoin each other; and
a display section for displaying the row-of-teeth image generated by the image-generating section.

15. A dental colorimetry system comprising:
an image-acquisition device for acquiring an image inside an oral cavity; and
a dental colorimetry apparatus for processing the image acquired by the image-acquisition device;
wherein the dental colorimetry apparatus comprises:
a first storage section storing a plurality of tooth images containing a plurality of target teeth constituting a row of the teeth and partial adjacent teeth adjacent to the target teeth in association with information about the positions of the plurality of target teeth in the row of the teeth, respectively;

a contour-line extracting section for extracting contour lines of the plurality of target teeth and the adjacent teeth, respectively, from the plurality of tooth images;

a rectangle-setting section for setting rectangles in the plurality of tooth images so as to include the contour lines of the plurality of target teeth extracted by the contour-line extracting section and so as to circumscribe at least both sides of the target teeth, respectively;

an image-generating section for generating a row-of-teeth image by arranging portions of the plurality of tooth images inside the rectangles based on the information about the positions of the plurality of target teeth in the row of the teeth so that the rectangles inscribe the contour lines of the adjacent teeth in the adjacent tooth images; and a display section for displaying the row-of-teeth image generated by the image-generating section.

16. A dental colorimetry method comprising:

extracting contour lines of teeth from images of a plurality of the teeth constituting a row of the teeth associated with information about the positions of the plurality of teeth in the row of the teeth, respectively;

setting rectangles in the images of the plurality of teeth so as to include the extracted contour lines and so as to circumscribe at least both sides of the teeth, respectively; and generating a row-of-teeth image by arranging the images of the plurality of teeth based on the information about the positions of the plurality of teeth in the row of the teeth so that the rectangles adjoin each other.

17. A dental colorimetry method comprising:

extracting contour lines of a plurality of target teeth and partial adjacent teeth adjacent to the target teeth from a plurality of tooth images containing the plurality of target teeth constituting a row of the teeth and the adjacent teeth and associated with information about the positions of the target teeth in the row of the teeth;

setting rectangles in the plurality of tooth images so as to include the extracted contour lines of the plurality of target teeth and so as to circumscribe at least both sides of the target teeth, respectively; and generating a row-of-teeth image by arranging portions of the tooth images inside the rectangles based on the information about the positions of the plurality of target teeth in the row of the teeth so that the rectangles inscribe the contour lines of the adjacent teeth in a plurality of the adjacent tooth images.

18. A non-transitory computer-readable recording medium storing a dental colorimetry program thereon for instructing a computer to execute a process comprising:

extracting contour lines of teeth from images of a plurality of the teeth constituting a row of the teeth associated with information about the positions of the plurality of teeth in the row of the teeth, respectively;

setting rectangles in the images of the plurality of teeth so as to include the extracted contour lines and so as to circumscribe at least both sides of the teeth, respectively; and generating a row-of-teeth image by arranging the images of the plurality of teeth based on the information about the positions of the plurality of teeth in the row of the teeth so that the rectangles adjoin each other.

19. A non-transitory computer-readable recording medium storing a dental colorimetry program thereon for instructing a computer to execute a process comprising:

extracting contour lines of a plurality of target teeth and partial adjacent teeth adjacent to the target teeth from a plurality of tooth images containing the plurality of target teeth constituting a row of the teeth and the adjacent teeth and associated with information about the positions of the target teeth in the row of the teeth;

setting rectangles in the plurality of tooth images so as to include the extracted contour lines of the plurality of target teeth and so as to circumscribe at least both sides of the target teeth, respectively; and generating a row-of-teeth image by arranging portions of the tooth images inside the rectangles based on the information about the positions of the plurality of target teeth in the row of the teeth so that the rectangles inscribe the contour lines of the adjacent teeth in a plurality of the adjacent tooth images.

20. The dental colorimetry apparatus according to claim 1, wherein the image-generating section generates teeth images so as to have smaller lateral widths farther away from a center of the row of teeth in a row-of-teeth direction.

21. The dental colorimetry system according to claim 14, wherein the image-generating section generates teeth images so as to have smaller lateral widths farther away from a center of the row of teeth in a row-of-teeth direction.

22. The dental colorimetry method according to claim 16, wherein generating the row-of-teeth image comprises generating teeth images so as to have smaller lateral widths farther away from a center of the row of teeth in a row-of-teeth direction.

23. The computer-readable recording medium according to claim 18, wherein generating the row-of-teeth image comprises generating teeth images so as to have smaller lateral widths farther away from a center of the row of teeth in a row-of-teeth direction.

24. The dental colorimetry apparatus according to claim 1, wherein the image-generating section changes a scale-down ratio of a tooth in a row-of-teeth direction depending on a viewpoint.

25. The dental colorimetry system according to claim 14, wherein the image-generating section changes a scale-down ratio of a tooth in a row-of-teeth direction depending on a viewpoint.

26. The dental colorimetry method according to claim 16, wherein generating the row-of-teeth image comprises changing a scale-down ratio of a tooth in a row-of-teeth direction depending on a viewpoint.

27. The computer-readable recording medium according to claim 18, wherein generating the row-of-teeth image comprises changing a scale-down ratio of a tooth in a row-of-teeth direction depending on a viewpoint.

\* \* \* \* \*